(12) United States Patent
Tan et al.

(10) Patent No.: US 9,458,460 B2
(45) Date of Patent: Oct. 4, 2016

(54) PHARMACEUTICAL COMPOSITIONS FOR TREATING CANCER

(75) Inventors: Patrick Tan, Singapore (SG); Tatiana Ivanova, Singapore (SG)

(73) Assignees: National University of Singapore, Singapore (SG); Singapore Health Services Pte Ltd., Singapore (SG)

( * ) Notice: Subject to any disclaimer, the term of this patent is extended or adjusted under 35 U.S.C. 154(b) by 241 days.

(21) Appl. No.: 14/130,226

(22) PCT Filed: Jun. 28, 2012

(86) PCT No.: PCT/SG2012/000232
§ 371 (c)(1),
(2), (4) Date: May 8, 2014

(87) PCT Pub. No.: WO2013/002733
PCT Pub. Date: Jan. 3, 2013

(65) Prior Publication Data
US 2015/0050360 A1    Feb. 19, 2015

(30) Foreign Application Priority Data
Jun. 29, 2011 (SG) .................................. 201104811

(51) Int. Cl.
| | |
|---|---|
| *A61K 31/70* | (2006.01) |
| *C07H 21/02* | (2006.01) |
| *C07H 21/04* | (2006.01) |
| *C12N 15/113* | (2010.01) |
| *A61K 45/06* | (2006.01) |
| *A61K 31/282* | (2006.01) |
| *A61K 31/555* | (2006.01) |
| *A61K 31/7105* | (2006.01) |
| *A61K 31/711* | (2006.01) |
| *A61K 33/24* | (2006.01) |
| *C12Q 1/68* | (2006.01) |
| *C12N 5/00* | (2006.01) |

(52) U.S. Cl.
CPC .......... *C12N 15/1136* (2013.01); *A61K 31/282* (2013.01); *A61K 31/555* (2013.01); *A61K 31/711* (2013.01); *A61K 31/7105* (2013.01); *A61K 33/24* (2013.01); *A61K 45/06* (2013.01); *C12Q 1/6886* (2013.01); *C12Q 2600/136* (2013.01)

(58) Field of Classification Search
None
See application file for complete search history.

(56) References Cited

U.S. PATENT DOCUMENTS
2003/0134790 A1    7/2003    Langenfeld

FOREIGN PATENT DOCUMENTS
| | | |
|---|---|---|
| WO | WO-2007/085497 | 8/2007 |
| WO | WO-2011/116212 | 9/2011 |

OTHER PUBLICATIONS

Deng et al., Cancer Letters vol. 281:220-231, 2009.*
"International Application No. PCT/SG2012/000232, International Search Report dated Sep. 19, 2012", 8 pgs.
Feeley, Brian T, et al., "Overexpression of noggin inhibits BMP-mediated growth of osteolytic prostate cancer lesions", Bone, 38(2), (Aug. 26, 2005), 154-66.
Laatio, Liisa, et al., "BMP-4 expression has prognostic significance in advanced serous ovarian carcinoma and is affected by cisplatin in OVCAR-3 cells", Tumour Biol., 32(5), (Jun. 15, 2011), 985-95.

* cited by examiner

*Primary Examiner* — Sean McGarry
(74) *Attorney, Agent, or Firm* — Schwegman Lundberg & Woessner, P.A.

(57) ABSTRACT

The present invention relates to a pharmaceutical composition comprising an anti-cancer drug and an inhibitor of bone morphogenetic protein 4 (BMP-4) or its gene expression. The present invention also relates to methods of treating cancer and prognostic methods.

8 Claims, 32 Drawing Sheets

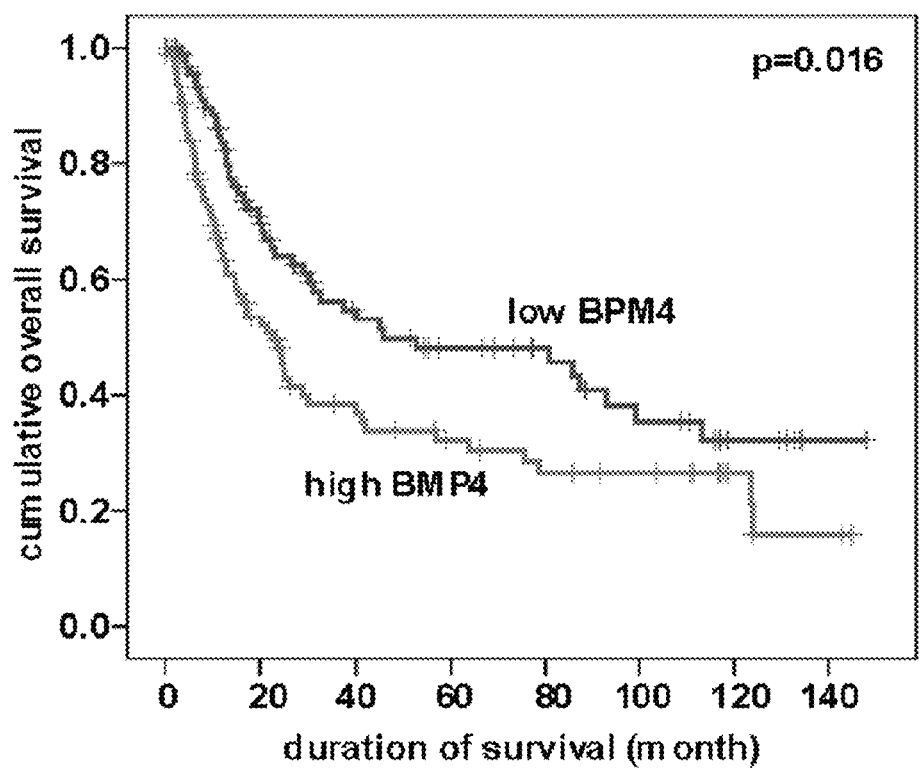

FIG. 11C

| β-value | S100A2 | \multicolumn{5}{c}{CpG sites} |
| | | 1 | 2 | 3 | 4 | 5 |
| | | -1266 | -1243 | -1186 | -1099 | -1091 |
| 0.67 | AZ521 | ● | ● | ● | ● | NA |
| 0.05 | Hs746T | ○ | ○ | ○ | ○ | NA |
| 0.04 | IM95 | ○ | ○ | ○ | ○ | NA |
| 0.10 | MKN1 | ○ | ○ | ○ | ○ | NA |
| 0.30 | MKN7 | ○ | ○ | ● | ○ | NA |
| 0.03 | MKN45 | ○ | ○ | ○ | ○ | NA |
| 0.03 | TMK1 | ○ | ○ | ○ | ○ | NA |
| 0.07 | YCC7 | ○ | ○ | ○ | ○ | NA |

YCC10

YCC16

FU97

YCC11

AZ521

MKN45

SEQUENCE LISTING

<160> NUMBER OF SEQ ID NOS: 24

<210> SEQ ID NO 1
<211> LENGTH: 22
<212> TYPE: DNA
<213> ORGANISM: Artificial Sequence
<220> FEATURE:
<223> OTHER INFORMATION: A Synthetic Primer - MS-PCR

<400> SEQUENCE: 1
gttcgagttc gtagttgtcg tc                                        22

<210> SEQ ID NO 2
<211> LENGTH: 25
<212> TYPE: DNA
<213> ORGANISM: Artificial Sequence
<220> FEATURE:
<223> OTHER INFORMATION: A Synthetic Primer - MS-PCR

<400> SEQUENCE: 2
cgatacatac tttctaatac ctccg                                     25

<210> SEQ ID NO 3
<211> LENGTH: 24
<212> TYPE: DNA
<213> ORGANISM: Artificial Sequence
<220> FEATURE:
<223> OTHER INFORMATION: A Synthetic Primer - MS-PCR

<400> SEQUENCE: 3
gtttgagttt gtagttgttg ttgg                                      24

<210> SEQ ID NO 4
<211> LENGTH: 27
<212> TYPE: DNA
<213> ORGANISM: Artificial Sequence
<220> FEATURE:
<223> OTHER INFORMATION: A Synthetic Primer - MS-PCR

<400> SEQUENCE: 4
caatacatac tttctaatac ctccaca                                27

<210> SEQ ID NO 5
<211> LENGTH: 21
<212> TYPE: DNA
<213> ORGANISM: Artificial Sequence
<220> FEATURE:
<223> OTHER INFORMATION: A Synthetic Primer - Bisulfite Sequencing

<400> SEQUENCE: 5
gttgttttta gttttgggaa g                                      21

<210> SEQ ID NO 6
<211> LENGTH: 25
<212> TYPE: DNA
<213> ORGANISM: Artificial Sequence
<220> FEATURE:
<223> OTHER INFORMATION: A Synthetic Primer - Bisulfite Sequencing

<400> SEQUENCE: 6
tcccataaat atttttaaaa aatac                                  25

<210> SEQ ID NO 7
<211> LENGTH: 22
<212> TYPE: DNA
<213> ORGANISM: Artificial Sequence
<220> FEATURE:
<223> OTHER INFORMATION: A Synthetic Primer - RT-PCR

<400> SEQUENCE: 7
tgtcaagaat catggactgt ta                                     22

<210> SEQ ID NO 8
<211> LENGTH: 23
<212> TYPE: DNA
<213> ORGANISM: Artificial Sequence
<220> FEATURE:
<223> OTHER INFORMATION: A Synthetic Primer - RT-PCR

<400> SEQUENCE: 8
ggcttcataa cctcataaat gtt                                    23

<210> SEQ ID NO 9
<211> LENGTH: 23
<212> TYPE: DNA
<213> ORGANISM: Artificial Sequence
<220> FEATURE:
<223> OTHER INFORMATION: A Synthetic Primer - RT-PCR

<400> SEQUENCE: 9
ccagagttta ctgccatgac gtt                                    23

<210> SEQ ID NO 10
<211> LENGTH: 22
<212> TYPE: DNA
<213> ORGANISM: Artificial Sequence
<220> FEATURE:

<223> OTHER INFORMATION: A Synthetic Primer - RT-PCR

<400> SEQUENCE: 10
caattgtagt tatttgtcca tt                                    22

<210> SEQ ID NO 11
<211> LENGTH: 23
<212> TYPE: DNA
<213> ORGANISM: Artificial Sequence
<220> FEATURE:
<223> OTHER INFORMATION: A Synthetic Primer - RT-PCR

<400> SEQUENCE: 11
gttcaccgat gcccagaagc att                                   23

<210> SEQ ID NO 12
<211> LENGTH: 23
<212> TYPE: DNA
<213> ORGANISM: Artificial Sequence
<220> FEATURE:
<223> OTHER INFORMATION: A Synthetic Primer - RT-PCR

<400> SEQUENCE: 12
ttaccaggtc caggcagaca gtt                                   23

<210> SEQ ID NO 13
<211> LENGTH: 23
<212> TYPE: DNA
<213> ORGANISM: Artificial Sequence
<220> FEATURE:
<223> OTHER INFORMATION: A Synthetic Primer - RT-PCR

<400> SEQUENCE: 13
gtcagagact ggagccatta ctt                                   23

<210> SEQ ID NO 14
<211> LENGTH: 24
<212> TYPE: DNA
<213> ORGANISM: Artificial Sequence
<220> FEATURE:
<223> OTHER INFORMATION: A Synthetic Primer - RT-PCR

<400> SEQUENCE: 14
ctcaatctgc tgagaccagt actt                                  24

<210> SEQ ID NO 15
<211> LENGTH: 25
<212> TYPE: DNA
<213> ORGANISM: Artificial Sequence
<220> FEATURE:
<223> OTHER INFORMATION: A Synthetic Primer - RT-PCR

<400> SEQUENCE: 15
aaactacagc gaactggaca cacat                                 25

<210> SEQ ID NO 16
<211> LENGTH: 23
<212> TYPE: DNA
<213> ORGANISM: Artificial Sequence
<220> FEATURE:
<223> OTHER INFORMATION: A Synthetic Primer - RT-PCR

<400> SEQUENCE: 16
ctttctgagc cactgtggtc ctt                                   23

-continued

```
<210> SEQ ID NO 17
<211> LENGTH: 21
<212> TYPE: DNA
<213> ORGANISM: Artificial Sequence
<220> FEATURE:
<223> OTHER INFORMATION: A Synthetic Primer - RT-PCR

<400> SEQUENCE: 17
cttgcaagcc atctgcggca t                                              21

<210> SEQ ID NO 18
<211> LENGTH: 20
<212> TYPE: DNA
<213> ORGANISM: Artificial Sequence
<220> FEATURE:
<223> OTHER INFORMATION: A Synthetic Primer - RT-PCR

<400> SEQUENCE: 18
tccatcagga actgtggcat                                                20

<210> SEQ ID NO 19
<211> LENGTH: 21
<212> TYPE: DNA
<213> ORGANISM: Artificial Sequence
<220> FEATURE:
<223> OTHER INFORMATION: A Synthetic Primer - RT-PCR

<400> SEQUENCE: 19
ttctctcaag acttacggtg t                                              21

<210> SEQ ID NO 20
<211> LENGTH: 21
<212> TYPE: DNA
<213> ORGANISM: Artificial Sequence
<220> FEATURE:
<223> OTHER INFORMATION: A Synthetic Primer - RT-PCR

<400> SEQUENCE: 20
cttcagttgt ctgtactgag t                                              21

<210> SEQ ID NO 21
<211> LENGTH: 19
<212> TYPE: DNA
<213> ORGANISM: Artificial Sequence
<220> FEATURE:
<223> OTHER INFORMATION: A Synthetic Primer - RT-PCR

<400> SEQUENCE: 21
tgaacgggaa gctcactgg                                                 19

<210> SEQ ID NO 22
<211> LENGTH: 20
<212> TYPE: DNA
<213> ORGANISM: Artificial Sequence
<220> FEATURE:
<223> OTHER INFORMATION: A Synthetic Primer - RT-PCR

<400> SEQUENCE: 22
tccaccaccc tgttgctgta                                                20

<210> SEQ ID NO 23
<211> LENGTH: 29
<212> TYPE: DNA
<213> ORGANISM: Artificial Sequence
<220> FEATURE:
<223> OTHER INFORMATION: A Synthetic shRNA
```

```
<400> SEQUENCE: 23
tgaggtgact cacctccatc agactcgga                              29

<210> SEQ ID NO 24
<211> LENGTH: 29
<212> TYPE: DNA
<213> ORGANISM: Artificial Sequence
<220> FEATURE:
<223> OTHER INFORMATION: A Synthetic shRNA

<400> SEQUENCE: 24
gccactcgct ctatgtggac ttcagcgat                              29
```

PHARMACEUTICAL COMPOSITIONS FOR TREATING CANCER

CROSS-REFERENCE TO RELATED APPLICATIONS

This application is a national stage application under 35 U.S.C. §371 of PCT/SG2012/000232, filed Jun. 28, 2012, and published as WO 2013/002733 A1 on Jan. 3, 2013, which claims the benefit of priority of Singapore patent application no. 201104811-3, filed Jun. 29, 2011, which applications and publication are incorporated by reference as if reproduced herein and made a part hereof in their entirety, and the benefit of priority of each of which is claimed herein.

FIELD OF THE INVENTION

The present invention relates to biochemistry and medical applications of biochemical molecules used for treating cancer.

BACKGROUND OF THE INVENTION

A cancer is a group of cells that has lost its normal control mechanisms resulting in unregulated growth. Cancerous cells are also called malignant cells and can develop from any tissue within any organ. As cancerous cells grow and multiply, they form a tumour that invades and destroys normal adjacent tissues. Cancerous cells from the primary site can also spread throughout the body.

One of the major treatments for cancer is chemotherapy which involves the use of drugs to destroy cancer cells. Chemotherapeutic drugs kill cancer cells by damaging the cellular DNA and are divided into drugs classes including but not limited to DNA cross-linkers, platinum complexes and antimetabolites. The choice, combination and dosage of chemotherapeutic drugs used depend on the type of cancer being treated. Unfortunately, not all cancers respond to chemotherapy and drug resistance to chemotherapy can also develop. It is known that different cancers employ a wide variety of mechanisms to elicit resistance to chemotherapeutic drugs. However, the factors that regulate tumour response to chemotherapy remain obscure.

There is therefore a need to provide an alternative therapy for treating cancer that overcomes, or at least ameliorates, one or more of the disadvantages described above.

SUMMARY OF THE INVENTION

According to a first aspect, there is provided a pharmaceutical composition comprising an anti-cancer drug and an inhibitor of bone morphogenetic protein 4 (BMP4) gene expression and/or an inhibitor of bone morphogenetic protein 4 (BMP4), wherein the anti-cancer drug excludes oxaliplatin and/or derivatives thereof.

According to a second aspect, there is provided a method of treating a patient suffering from cancer by administering a pharmaceutical composition as defined above.

According to a third aspect, there is provided a use of a pharmaceutical composition as defined above in the manufacture of a medicament for treating cancer.

According to a fourth aspect, there is provided a method of sensitizing a patient suffering from cancer to a treatment with one or more anti-cancer drugs, wherein the anti-cancer drug excludes oxaliplatin and/or derivatives thereof by inhibiting expression of bone morphogenetic protein 4 (BMP4) gene and/or by inhibiting bone morphogenetic protein 4 (BMP4).

According to a fifth aspect, there is provided a method of re-sensitizing a patient suffering from cancer and not responding to a treatment with one or more anti-cancer drugs, wherein the anti-cancer drug excludes oxaliplatin and/or derivative thereof by inhibiting expression of bone morphogenetic protein 4 (BMP4) gene or by inhibiting bone morphogenetic protein 4 (BMP4).

According to a sixth aspect, there is provided an in vitro prognostic method of determining the receptiveness of a patient suffering from cancer to the treatment with an anti-cancer drug, wherein the method comprises identifying the gene expression level of BMP4 or a functional variant thereof, or the level of BMP4 in cancer cells obtained from the patient, and wherein an increased gene expression or presence of BMP4 or a functional variant thereof or increased level of BMP4 indicates that the patient is receptive for treatment with an anti-cancer drug.

According to a seventh aspect, there is provided a method of determining a gene or genes involved in anti-cancer drug resistance, wherein the method comprises:
  determining the anti-cancer drug response of a patient to the treatment with the anti-cancer drug;
  determining transcriptomic and genomic DNA methylation profiles of the patient treated with the anti-cancer drug; and
  correlating the anti-cancer drug response data with data obtained from the transcriptomic and genomic DNA methylation profiles to identify the gene or genes which expression is increased or decreased in patients expressing an anti-cancer drug resistance compared to those patients who do not show an anti-cancer drug resistance;
  wherein the gene or genes having only an increased or decreased expression in patients who show an anti-cancer drug resistance is/are the gene or genes involved in anti-cancer drug resistance.

BRIEF DESCRIPTION OF THE DRAWINGS

The invention will be better understood with reference to the detailed description when considered in conjunction with the non-limiting examples and the accompanying drawings, in which:

FIG. 1 comprises FIGS. 1A, 1B and 1C. As seen in FIG. 1B, significantly higher capase-3 activation levels were observed in cisplatin sensitive cell lines, YCC11 and SCH, compared to cisplatin resistant cell lines AGS and AZ521.

FIG. 2 comprises FIGS. 2A, 2B and 2C.

FIG. 3 comprises FIGS. 3A, 3B, 3C and 3D.

FIG. 4 comprises FIGS. 4A, 4B and 4C.

FIG. 5 comprises FIGS. 5A, 5B and 5C.

FIG. 6 comprises FIGS. 6A, 6B and 6C. FIG. 6C shows the Kaplan-Meier plot of overall survival in gastric cancer patients stratified BMP4 gene expression. Patients were divided into two groups based upon the median BMP4 expression level. FIG. 6C shows a significant survival difference between these two groups.

FIG. 7 comprises FIGS. 7A and 7B.

FIG. 11A to 11C show the experimental validation of GoldenGate DNA methylation. FIGS. 11A, 11B and 11C show bisulphate-based sequence analysis of APC, BRCA1 and S100A2 respectively. Each circle indicates a CpG site in the primary DNA sequence, each line of circles represents analysis of total PCR product generated from bisulfite-treated DNA of a cell line. White circles represent unmethylated CpG sites, black circles represent methylated CpG sites and grey circles represent partially methylated CpG site. From FIGS. 11A to 11C, it can be seen that CpG probes were consistently associated with increased DNA methylation.

FIG. 13 comprises FIGS. 13A, 13B and 13C.

DETAILED DESCRIPTION OF THE PRESENT INVENTION

Figure 1A:
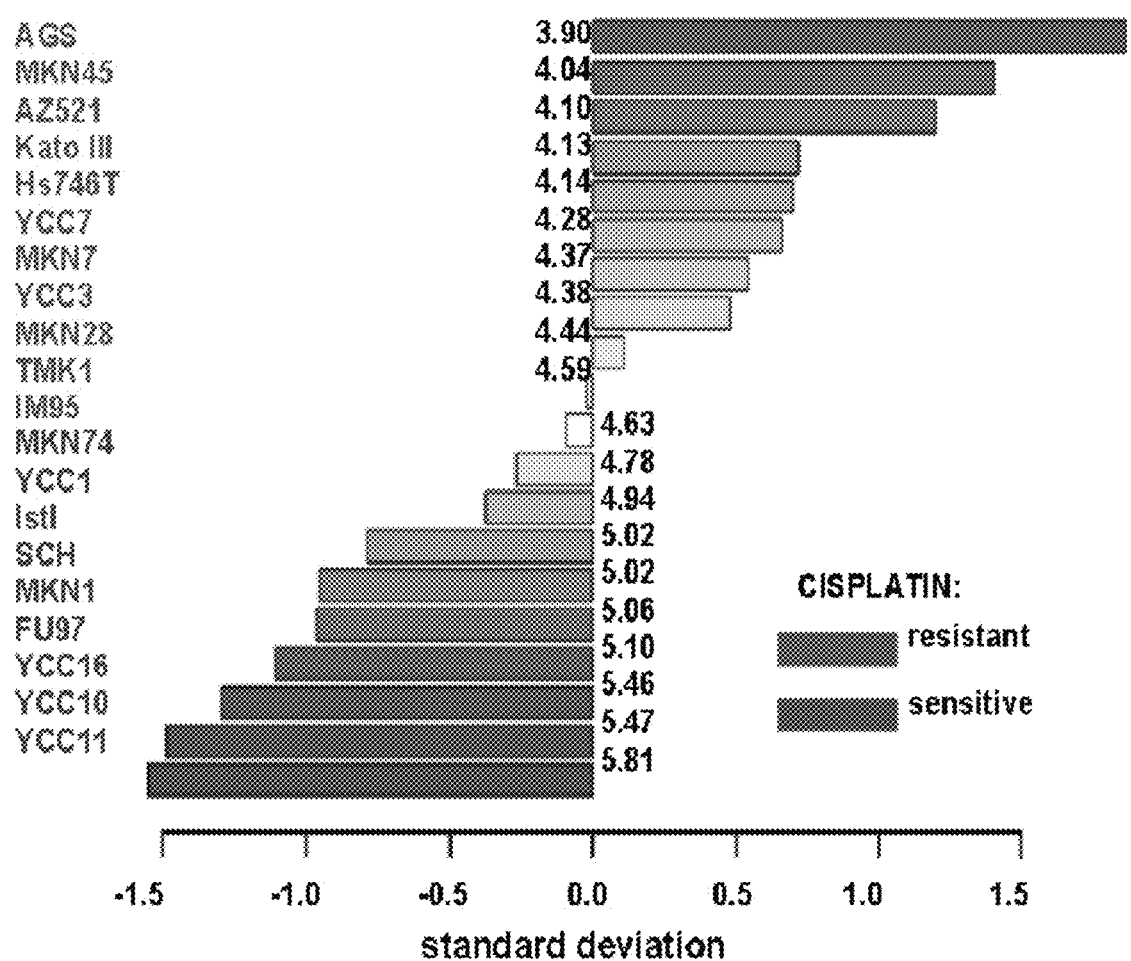
FIG. 1A shows the effects of cisplatin on the proliferation of 20 cancer cell lines. Cisplatin is a commonly used anti-cancer drug. Cell lines were treated with increasing concentrations of cisplatin and the concentration of cisplatin required to cause 50% growth inhibition was determined. From FIG. 1A, it can be seen that there are striking variations in the levels of cisplatin sensitivity between different cancer cell lines.

As it is known in the art it is sometimes possible that a cancer treatment using commonly known anti-cancer drugs is not successful due to the fact that the cancer cells are resistant or develop a resistance to the anti-cancer drug or combination of anti-cancer drugs used.

Therefore, the present invention provides in a first aspect a pharmaceutical composition comprising an anti-cancer drug and an inhibitor of bone morphogenetic protein 4 (BMP4) gene expression and/or an inhibitor of bone morphogenetic protein 4 (BMP4).

It has been found that BMP4 gene hypermethylation is associated with BMP4 gene silencing and strongly correlated with sensitivity to certain anti-cancer drugs, such as platinum complexes. Thus, further experiments indicated that a pre-treatment or combination treatment of a patient suffering from cancer with a BMP4 gene/BMP4 protein inhibitor alone or in combination with one or more anti-cancer drugs, for example re-sensitizes an anti-cancer drug resistant tumor of a patient for further treatment or avoids occurrence of such an anti-cancer drug resistance.

Accordingly, pre-treatment or combination treatment of a patient suffering from cancer with a inhibitor of the BMP4 receptor and/or an inhibitor of pathways activated by BMP4 that lie downstream of BMP4 would probably also re-sensitize an anti-cancer drug resistant tumor of a patient for further treatment or avoid occurrence of such an anti-cancer drug resistance.

As used herein, a pharmaceutical composition refers to a mixture of one or more of the compounds described herein, or physiologically/pharmaceutically acceptable salts or prodrugs thereof, with other chemical components, such as physiologically/pharmaceutically acceptable carriers and excipients. The purpose of a pharmaceutical composition is to facilitate administration of a compound to an organism.

As used herein, the inhibitor of BMP4 gene and/or protein in the pharmaceutical composition may be administered before, shortly before, during, shortly after or after administration of the anti-cancer drug.

As used herein, shortly refers to 1 day, 12 hours, 6 hours, 5 hours, 4 hours, 3 hours, 2 hours, 1 hour, 30 minutes, 15 minutes, 5 minutes or 1 minute.

As used herein, the term "pharmaceutically acceptable carrier" refers to media generally accepted in the art for the delivery of biologically active agents, i.e. the disclosed inhibitor alone or in combination with any of the disclosed compounds in the context of the specification, to mammals, e.g. humans. Such carriers are generally formulated according to a number of factors well within the purview of those of ordinary skill in the art to determine and account for. These include, without limitation, the type and nature of the active agent, being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Non-limiting examples of a pharmaceutically acceptable carrier are hyaluronic acid and salts thereof, and microspheres (including, but not limited to, poly(D,L)-lactide-co-glycolic acid copolymer (PLGA), poly(L-lactic acid) (PLA), poly(caprolactone) (PCL) and bovine serum albumin (BSA)).

The term "excipient" refers to a pharmaceutically acceptable additive, other than the active ingredient, included in a formulation and having different purposes depending, for example, on the nature of the drug, and the mode of administration. Examples of excipients include, but are not limited to, carriers, co-solvents, stabilizing agents, solubilizing agents and surfactants, buffers, antioxidants, tonicity agents, bulking agents, lubricating agents, emulsifiers, suspending or viscosity agents, antibacterial agents, chelating agents, preservatives, sweeteners, perfuming agents, flavoring agents, administration aids, and combinations thereof. Some of the excipients or additives may have more than one possible function or use, depending on their properties and the nature of the formulation.

As used herein, the term anti-cancer drug refers to drugs used to treat malignancies or cancerous growths that may be used alone or in combination with other treatments. Examples of anti-cancer drugs include but are not limited to platinum complexes.

As used in the context of the specification, the term platinum complex refers to compounds comprising platinum that form intrastrand and interstrand cross-links between purines on DNA. Examples include but are not limited to cisplatin (also known as cis-diamminedichloroplatinum (II) or CDDP), carboplatin and derivatives thereof. In one specific example platinum complexes excludes oxaliplatin and/or derivatives thereof.

As used herein, the phrase 'derivatives thereof' in relation to platinum complexes refers to platinum containing compound comprising different ligands.

As used in the context of the specification, the phrases "inhibiting the BMP4 gene" or "inhibitor of the BMP4 gene", or variants thereof, mean that the expression of the BMP4 gene is decreased or absent. Further, in the context of the specification, the phrases "inhibiting the BMP4 protein" or "inhibitor of the BMP4 protein", or variants thereof, mean that the activity of the BMP4 protein is decreased or absent. Absent means that there is completely no expression of the BMP4 gene or activity of the BMP4 protein.

The inhibitor of any of the genes referred to herein may comprise at least one oligonucleotide. The oligonucleotide may be an interfering ribonucleic acid (iRNA). The term "oligonucleotide" generally refers to a single-stranded nucleotide polymer made of more than 2 nucleotide subunits covalently joined together. Preferably between 10 and 100 nucleotide units are present, most preferably between 12 and 50 nucleotides units are joined together. The sugar groups of the nucleotide subunits may be ribose, deoxyribose or modified derivatives thereof such as 2'-O-methyl ribose. The nucleotide subunits of an oligonucleotide may be joined by phosphodiester linkages, phosphorothioate linkages, methyl phosphonate linkages or by other rare or non-naturally-occurring linkages that do not prevent hybridization of the oligonucleotide. Furthermore, an oligonucleotide may have uncommon nucleotides or nonnucleotide moieties. An oligonucleotide, as defined herein, is a nucleic acid, such as deoxyribonucleic acid (DNA) or ribonucleic acid (RNA), or have a combination of ribo- and deoxyribonucleotides covalently linked.

The interfering ribonucleic acid may be a small interfering ribonucleic acid (siRNA) or small hairpin ribonucleic acid (shRNA) or micro ribonucleic acid (miRNA).

Modified oligonucleotides used as interfering ribonucleic acids may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particular examples include, but are not limited to $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other exemplary oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One exemplary modification includes 2'-methoxyethoxy (2'-O—$CH_2CH_2OCH_3$, also known as 2'-O-(2-methoxyethyl) or 2'-MOE), i.e., an alkoxyalkoxy group.

As used herein, the term "siRNA" refers to a ribonucleic acid (RNA) or RNA analog comprising between about 10 to 50 nucleotides (or nucleotide analogs) capable of directing or mediating the RNA interference pathway. These molecules can vary in length and can contain varying degrees of complementarity to their target messenger RNA (mRNA) in the antisense strand. The term "siRNA" includes duplexes of two separate strands, i.e. double stranded RNA, as well as single strands that can form hairpin structures comprising of a duplex region. The siRNA may have a length of between about 10 to 50 nucleotides, or between about 15 to 50 nucleotides, or between about 20 to 50 nucleotides, or between about 25 to 50 nucleotides, or between about 30 to 50 nucleotides, or between about 35 to 50 nucleotides, or between about 40 to 50 nucleotides, or between about 10 to 45 nucleotides, or between about 10 to 40 nucleotides, or between about 10 to 35 nucleotides, or between about 10 to 30 nucleotides, or between about 10 to 25 nucleotides, or between about 10 to 20 nucleotides, or between about 15 to 50 nucleotides, or between about 15 to 35 nucleotides, or between about 15 to 30 nucleotides, or between about 15 to 25 nucleotides. In one embodiment, the siRNA has a length of between 15 to 30 nucleotides.

The application of siRNA to down-regulate the activity of its target mRNA is known in the art. In some embodiments, mRNA degradation occurs when the anti-sense strand, or guide strand, of the siRNA directs the RNA-induced silencing complex (RISC) that contains the RNA endonuclease Ago2 to cleave its target mRNA bearing a complementary sequence.

Accordingly, the siRNA may be complementary to any portion of varying lengths on the BMP4 gene. The siRNA may also be complementary to the sense strand and/or the anti-sense strand of the BMP4 gene. Accordingly, siRNA treatment may be used to silence the BMP4 gene, thereby depleting the BMP4 protein downstream.

The siRNA may be directed against fragments of the nucleic acid transcribed from the BMP4 gene. Accordingly, the siRNA may comprise a sequence that is complementary to any fragment of the BMP4 gene or functional variants thereof. Such functional variants thereof may comprise at least one modified or substituted nucleotide. Functional modifications and/or substitutions of the siRNA may be performed by methods known in the art.

The term "shRNA", as used herein, refers to a unimolecular RNA that is capable of performing RNAi and that has a passenger strand, a loop and a guide strand. The passenger and guide strand may be substantially complementary to each other. The term "shRNA" may also include nucleic acids that contain moieties other than ribonucleotide moieties, including, but not limited to, modified nucleotides, modified internucleotide linkages, non-nucleotides, deoxynucleotides, and analogs of the nucleotides mentioned thereof. In one embodiment, the shRNA comprises the sequence selected from the group consisting of 5'-TGAG-GTGACTCACCTCCATCAGACTCGGA-3' (SEQ ID NO. 23) and 5'-GCCACTCGCTCTATGTGGACTTCAGCGAT-3' (SEQ ID NO. 24), or functional variants thereof.

miRNAs down-regulate their target mRNAs. The term "miRNA" generally refers to a single stranded molecule, but in specific embodiments, may also encompass a region or an additional strand that is partially (between 10% and 50% complementary across length of strand), substantially (greater than 50% but less than 100% complementary across length of strand) or fully complementary to another region of the same single-stranded molecule or to another nucleic acid. Thus, nucleic acids may encompass a molecule that comprises one or more complementary or self-complementary strand(s) or "complements" of a particular sequence comprising a molecule. For example, precursor miRNA may have a self-complementary region, which is up to 100% complementary. miRNA probes or oligonucleotides of the invention can include, can be or can be at least 60%, 65%, 70%, 75%, 80%, 85%, 90%, 95%, 96%, 97%, 98%, 99% or 100% complementary to their target.

An inhibitor of BMP4 protein is a protein or small organic or inorganic molecule and may include a member of the BMP antagonist family. Proteins of this family contain cystine knots and typically form homo- and heterodimers.

Examples of BMP antagonists include but are not limited to noggin, chordin and gremlin. Noggin (NOG) is a secreted polypeptide that is encoded by the NOG gene. Noggin binds to members of the TGF-β superfamily of signaling proteins that include BMP4 and inactivates them. Noggin plays a crucial role in bone development, joint development and neural tube fusion. Chordin is a secreted polypeptide that is encoded by the CHRD gene. Chordin inactivates BMP4 by binding to BMP4 thereby preventing BMP4 from binding to its receptors. Gremlin is a glycoprotein that binds to BMPs and is important in limb development.

Anti-cancer drugs, such as platinum complexes are known to be useful for the treatment of different kinds of cancers. Exemplary kinds of cancer include, but are not limited to lung cancer, testicular cancer, breast cancer, colon cancer, ovarian cancer, head and neck cancer, esophageal cancer or gastric cancer. All of these cancer types are known to be treatable with anti-cancer drugs based on or including platinum complexes and are also known to develop resistances against the anti-cancer drugs used to treat these types of cancers.

As used herein, lung cancer refers to cancer that begins in the lung including but not limited to non-small cell lung cancer and small cell lung cancer.

As used herein, testicular cancer refers to cancer that starts in the testicles, including but not limited to seminomas and non-seminomas.

As used herein, breast cancer refers to cancer that starts in the tissue of the breast, including but not limited to ductal carcinoma and lobular carcinoma.

As used herein, colon cancer refers to cancer that starts in the large intestine or the rectum, including but not limited to carcinoma, lymphoma, carcinoid tumours, melanoma and sarcomas.

As used herein, ovarian cancer refers to cancer that starts in the ovaries, including but not limited to epithelial tumours, germ cell tumours and stromal tumours.

As used herein, head and neck cancer refers to a group of cancers that starts in the upper aerodigestive tract, including but not limited to the lip, oral cavity, nasal cavity, paranasal sinuses, pharynx, and larynx.

As used herein, esophageal cancer refers to cancer that starts in the esophagus, including but not limited to squamous cell carcinoma and adenocarcinoma.

As used herein, gastric cancer refers to cancer that starts in the stomach, including but not limited to adenocarcinoma, soft tissue sarcoma, lymphoma and carcinoid tumours.

As used herein, the term anti-gastric cancer drug refers to drugs used to treat malignancies or cancerous growths of the stomach.

The disclosed pharmaceutical composition may be used to treat a patient suffering from cancer. As such, in some embodiments, there is provided a method of treating a patient suffering from cancer by administering the disclosed pharmaceutical composition. As used herein, the terms "administering" or "administration", or grammatical variants thereof, refer to the delivery of the disclosed pharmaceutical composition to an organism for the purpose of treatment of cancer.

In some embodiments, there is provided a use of the disclosed pharmaceutical composition in the manufacture of a medicament for treating cancer. As used herein, the term "treating" refers to a method of alleviating or abrogating the abnormal condition in the organism.

In one embodiment, there is provided a method of sensitizing a patient suffering from cancer to treatment with anti-cancer drugs by inhibiting expression of BMP4 gene and/or inhibiting BMP4 protein. As used herein, the term sensitizing refers to a process of rendering a subject receptive to a treatment.

As used herein, inhibiting expression of BMP4 gene and/or BMP4 protein may be performed before, shortly before, during, shortly after and after treatment or administration with anti-cancer drugs in a patient suffering from cancer.

As used herein, shortly refers to 1 day, 12 hours, 6 hours, 5 hours, 4 hours, 3 hours, 2 hours, 1 hour, 30 minutes, 15 minutes, 5 minutes or 1 minute.

In one embodiment, there is provided a method of re-sensitizing a patient suffering from cancer and not responding to treatment with anti-cancer drugs by inhibiting expression of BMP4 gene and/or inhibiting BMP4 protein. As used herein, the term re-sensitizing refers to a process of restoring responsiveness to a treatment in a subject who was receptive to a treatment but who is no longer receptive to a treatment due to the fact that the patient or the tumor cells of the patient developed a resistance against the anti-cancer drug used for treating the cancer.

As used herein, inhibiting expression of BMP4 gene and/or BMP4 protein may be performed before, shortly before, during, shortly after and after treatment with anti-cancer drugs in a patient suffering from cancer and not responding to treatment or administration with anti-cancer drugs.

As used herein, shortly refers to 1 day, 12 hours, 6 hours, 5 hours, 4 hours, 3 hours, 2 hours, 1 hour, 30 minutes, 15 minutes, 5 minutes or 1 minute.

Accordingly, to aid in determining the receptiveness of a patient suffering from cancer to treatment with an anti-cancer drug, there is provided in one embodiment an in vitro prognostic method of determining the receptiveness of a patient suffering from cancer to the treatment with an anti-cancer drug, wherein the method comprises identifying the gene expression level of BMP4 or a functional variant thereof, or the level of BMP4 in cancer cells obtained from the patient, and wherein an increased gene expression or presence of BMP4 or a functional variant thereof or increased level of BMP4 indicates that the patient is receptive for treatment with an anti-cancer drug. The increase in gene expression or presence of BMP4 or a functional variant thereof or increased level of BMP4 as used in the context of the specification, is determined by comparison to a control, wherein the control is the level of gene expression or presence of BMP4 or a functional variant thereof and/or level of BMP4 protein in normal non-cancerous tissue from the same patient or the average level of gene expression or presence of BMP4 or a functional variant thereof and/or level of BMP4 protein in a group of individuals or the average level of expression of housekeeping genes and/or proteins.

As used herein, the term housekeeping genes and housekeeping proteins refer to genes and proteins whose expression remain relatively constant and include but are not limited to GAPDH and β-actin.

The term "prognosis", or grammatical variants thereof, as used herein refers to a prediction of the probable course and outcome of a clinical condition or disease. A prognosis of a patient is usually made by evaluating factors or symptoms of a disease that are indicative of a favorable or unfavorable course or outcome of the disease. The term "prognosis" does not refer to the ability to predict the course or outcome of a condition with 100% accuracy. Instead, the term "prognosis" refers to an increased probability that a certain course or outcome will occur; that is, that a course or outcome is more likely to occur in a patient exhibiting a given condition, when compared to those individuals not exhibiting the condition.

By the term "suffering from cancer", it is meant that the patient has already been diagnosed, or is suspected to be suffering from cancer.

As used herein, the term functional variant thereof of the BMP4 gene within the context of the specification refers to genes which possess a biological activity (either functional or structural) that is substantially similar to the BMP4 gene disclosed herein. Functional variants of BMP4 protein may be construed similarly to refer to a protein that is altered by one or more amino acids. The term "functional variant" also includes a fragment, a variant based on the degenerative nucleic acid code or a chemical derivative. A functional variant may have conservative changes, wherein a substituted amino acid or nucleic acid has similar structural or chemical properties to the replaced amino acid/nucleic acid, e.g. replacement of leucine with isoleucine. A functional variant may also have non-conservative changes, e.g. replacement of a glycine with a tryptophan, or a deletion and/or insertion of one or more amino acids, or a deletion and/or insertion of one or more nucleic acids. It is understood that the functional variant at least partially retains its biological activity, e.g. function, of the BMP4 gene or protein, or even exhibits improved biological activity.

Examples of functional variants of the BMP4 gene includes, but is not limited to genes having a sequence identity of about 60% or 70% or 80% or 90% or 92%, or 95%, or 98% or 99% to native BMP4 gene (Accession No. NM_001202 and NM_130850, respectively).

Examples of functional variants of the BMP4 protein includes, but is not limited to proteins having an amino acid sequence identity of 90% or 92%, or 95%, or 98% or 99% to the native BMP4 protein (Accession No. ACB21039).

In one embodiment, there is provided a method of determining a gene or genes involved in anti-cancer drug resistance, wherein the method comprises:
  determining the anti-cancer drug response of a patient to the treatment with the anti-cancer drug;
  determining transcriptomic and genomic DNA methylation profiles of the patient treated with the anti-cancer drug; and
  correlating the anti-cancer drug response data with data obtained from the transcriptomic and genomic DNA methylation profiles to identify the gene or genes which expression is increased or decreased in patients expressing an anti-cancer drug resistance compared to those patients who do not show an anti-cancer drug resistance;
  wherein the gene or genes having only an increased or decreased expression in patients who show an anti-cancer drug resistance is/are the gene or genes involved in anti-cancer drug resistance.

As used herein, anti-cancer drug resistance refers to the reduction in effectiveness of an anti-cancer drug in treating cancer. The reduction in effectiveness may be due to mechanisms employed by cancer cells including but not limited to reducing local drug concentrations by decreased drug import, increased detoxification and increased drug efflux, alterations in the expression of mismatch repair and nucleotide excision repair proteins, positivity to vascular endothelial growth factor (VEGF), signaling pathways such as NF-kB, c-ABL, JNK and p73 and aberrant patterns of DNA methylation.

As used herein, the term "transcriptome", "transcriptomic" or grammatical variants thereof refer to the set of all RNA molecules, including messenger RNA (mRNA), ribosomal RNA (rRNA), transfer RNA (tRNA) and other non-coding RNA produced in one or a population of cells.

As used herein, the term genomic DNA refers to the total genetic DNA in a cell or a population of cells and includes coding and non-coding DNA.

As used herein, the term DNA methylation profile refers to the presence or absence of a methyl group at the 5 position of the cytosine pyrimidine ring or 6 nitrogen of the adenosine purine ring in DNA.

As used herein, the cell lines AGS, KATO III and Hs746T are gastric cancer cell lines from the American Type Culture Collection. FU97, Ist1, MKN1, MKN7, MKN74, MKN28, MKN45, IM95, TMK1 and AZ521 are gastric cancer cell lines from the Japan Health Science Research Resource Bank. SCH is a gastric cancer cell line from Cancer Sciences Institute of Singapore. YCC1, YCC3, YCC7, YCC10, YCC11 and YCC16 are from Yonsei Cancer Centre, South Korea.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Non-limiting examples of the invention and comparative examples will be further described in greater detail by reference to specific Examples, which should not be construed as in any way limiting the scope of the invention.

The following Examples were carried out based on the fact that amongst chemotherapies, the platinum-complex cisplatin is widely used and a mainstay of anti-cancer therapy. It is therefore possible to perform cellular and genetic studies based on platinum-complex based anti-cancer drugs, such as cisplatin, thereby identifying corresponding mechanisms applicable with other anti-cancer drugs.

Table 1 shows the sequences of oligonucleotides used in this disclosure.

TABLE 1

The sequences of the oligonucleotides used in the disclosure.

| oligonucleotide | Sequence (5'-3') |
|---|---|
| MS-PCR | |
| BMP4-123MetFw | GTTCGAGTTCGTAGTTGTCGTC (SEQ ID NO: 1) |
| BMP4-123MetRv | CGATACATACTTTCTAATACCTCCG (SEQ ID NO: 2) |
| BMP4-123UnMetFw | GTTTGAGTTTGTAGTTGTTGTTGG (SEQ ID NO: 3) |
| BMP4-123UnMetRv | CAATACATACTTTCTAATACCTCCACA (SEQ ID NO: 4) |
| bisulfate sequence | |
| BMP4-199Fw | GTTGTTTTTAGTTTTGGGAAG (SEQ ID NO: 5) |
| BMP4-199Rv | TCCCATAAATATTTTTAAAAAATAC (SEQ ID NO: 6) |
| RT PCR | |
| BMP4-Fw | TGTCAAGAATCATGGACTGTTA (SEQ ID NO: 7) |
| BMP4-Rv | GGCTTCATAACCTCATAAATGTT (SEQ ID NO: 8) |
| CDH2-Fw | CCAGAGTTTACTGCCATGACGTT (SEQ ID NO: 9) |
| CDH2-Rv | CAATTGTAGTTATTTGTCCATT (SEQ ID NO: 10) |
| DSP-Fw | GTTCACCGATGCCCAGAAGCATT (SEQ ID NO: 11) |
| DSP-Rv | TTACCAGGTCCAGGCAGACAGTT (SEQ ID NO: 12) |
| KRT18-Fw | GTCAGAGACTGGAGCCATTACTT (SEQ ID NO: 13) |
| KRT18-Rv | CTCAATCTGCTGAGACCAGTACTT (SEQ ID NO: 14) |
| SLUG-Fw | AAACTACAGCGAACTGGACACACAT (SEQ ID NO: 15) |
| SLUG-Rv | CTTTCTGAGCCACTGTGGTCCTT (SEQ ID NO: 16) |
| DSG2-Fw | CTTGCAAGCCATCTGCGGCAT (SEQ ID NO: 17) |
| DSG2-Rv | TCCATCAGGAACTGTGGCAT (SEQ ID NO: 18) |
| TLN1-Fw | TTCTCTCAAGACTTACGGTGT (SEQ ID NO: 19) |
| TLN1-Rv | CTTCAGTTGTCTGTACTGAGT (SEQ ID NO: 20) |
| GAPDH-Fw | TGAACGGGAAGCTCACTGG (SEQ ID NO: 21) |
| GAPDH-Rv | TCCACCACCCTGTTGCTGTA (SEQ ID NO: 22) |
| shRNA | |
| BMP4 shRNA 1 | TGAGGTGACTCACCTCCATCAGACTCGGA (SEQ ID NO: 23) |
| BMP4 shRNA 2 | GCCACTCGCTCTATGTGGACTTCAGCGAT (SEQ ID NO: 24) |

Example 1

This example demonstrates the in vitro responses of gastric cancer (GC) cell lines to cisplatin.

Figure 8:
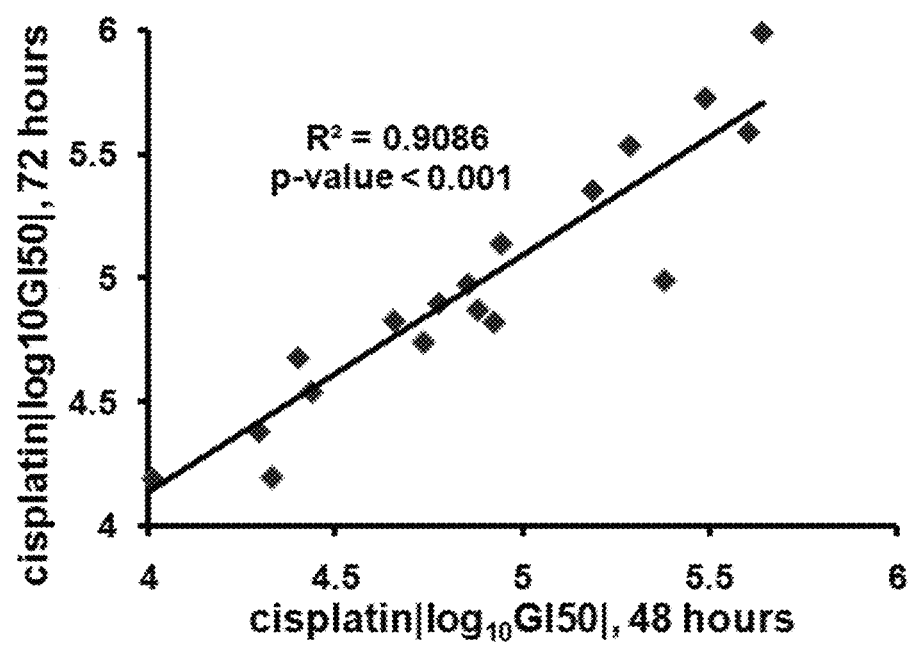
FIG. 8 shows cisplatin inhibits proliferation in 20 cell lines similarly at different time points. Each point represents a cell line.

20 GC cell lines were treated with increasing concentrations of cisplatin, from 0.1 µM to 1 mM. For each line, the cisplatin GI50, referring to the concentration of cisplatin required to cause 50% growth inhibition at 48 hrs. Striking variations in the levels of cisplatin sensitivity between different lines were observed as shown in FIG. 1A. YCC11 cells exhibited the greatest cisplatin sensitivity (mean GI50=1.5 µM) while AGS cells were the most resistant (mean GI50=126 µM), indicating a difference in GI50 of approximately 100 fold between the two extremes. Similar results were observed when the drug incubation times were extended from 48 hrs to 72 hrs (p-value≤0.001) as shown in FIG. 8.

Accordingly, these results demonstrate that distinct cell lines can exhibit varying sensitivities to cisplatin in vitro.

Figure 1B:
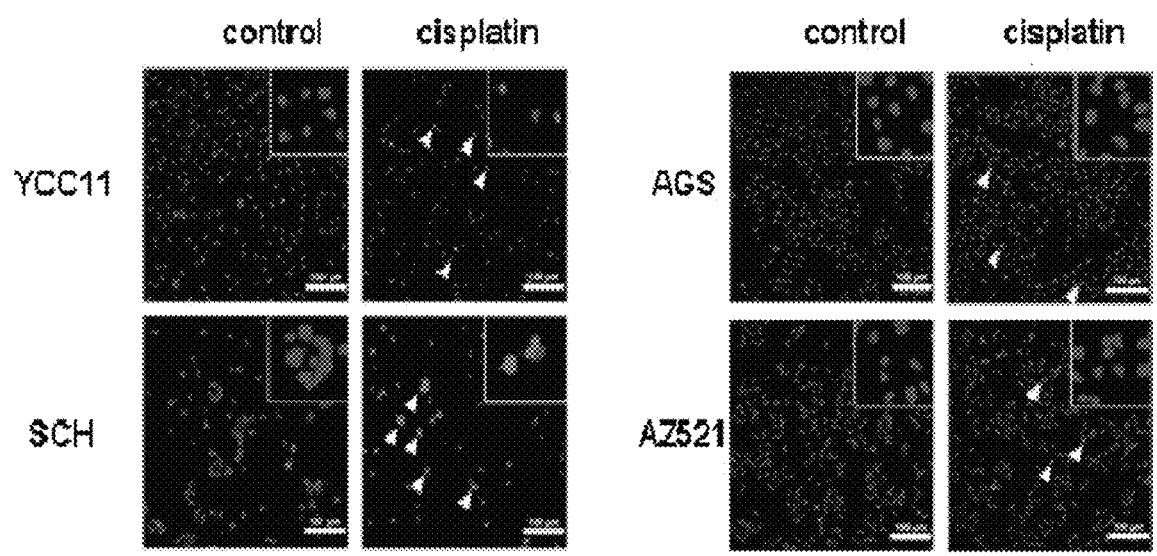
FIG. 1B shows cisplatin-mediated caspase 3 activation of two cisplatin sensitive and two cisplatin resistant cell lines treated with cisplatin.
Figure 1C:
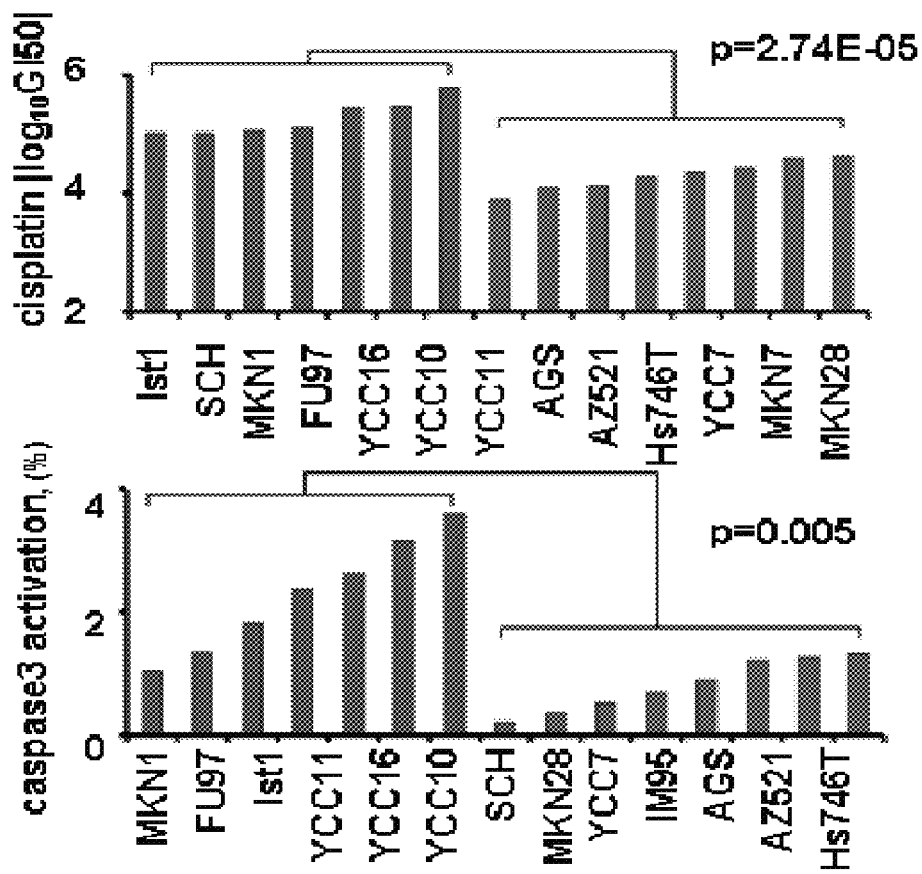
FIG. 1C shows the correlation between cisplatin induced proliferation inhibition with caspase 3 activation. The upper graph shows the proliferation inhibition of cisplatin sensitive and resistant cell lines while the bottom graph shows the percentage of caspase 3 activation in the same cell lines. It can be seen from FIG. 1C that there is a significant difference between cisplatin sensitive and resistant cell lines. This shows that inhibition of proliferation by cisplatin is significantly associated with apoptosis induction.

The reason for cell growth inhibition caused by cisplatin was determined using high-content screening (HCS), a cell-based technology allowing biological responses to be measured at the single-cell level, to quantify levels of caspase-3 activation in GC cells after cisplatin treatment. Five distinct morpho-cellular parameters were quantified for alterations induced by cisplatin—caspase3 activation, nuclear size, nuclear condensation, nuclear morphology and nuclear ellipticity. Significantly higher caspase-3 activation levels were observed in lines defined as cisplatin-sensitive by their GI50 values compared to cisplatin-resistant lines (p-value=0.005). These results are shown in FIGS. 1B and 1C.

Figure 9:
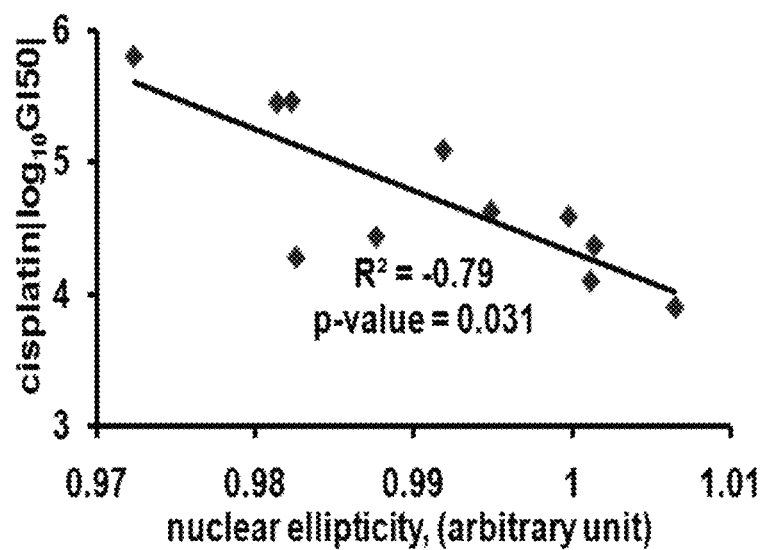
FIG. 9 shows the effect of cisplatin on nuclear ellipticity in cell lines. As can be seen from FIG. 9, there are significant changes in nuclear ellipticity after cisplatin treatment which is inversely correlated to caspase 3 activation.
Figure 9:
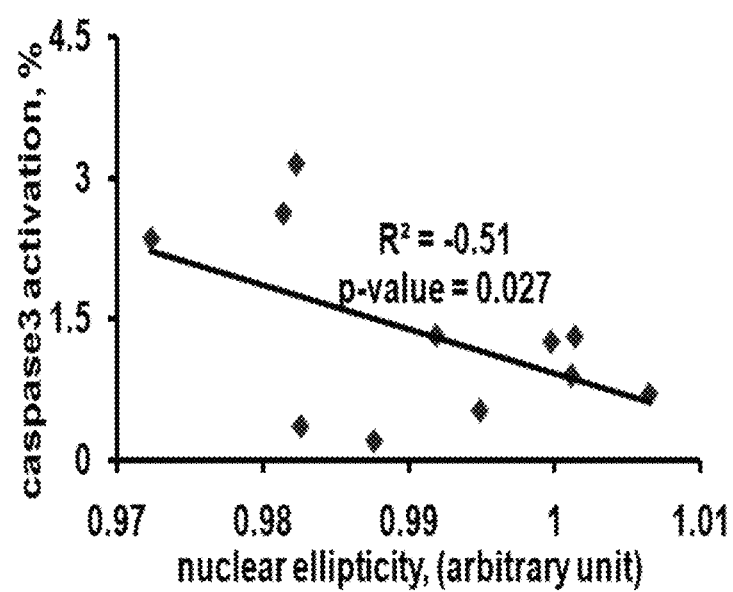

Significant changes in nuclear ellipticity were also observed in the top four sensitive lines compared to resistant lines after cisplatin treatment (p-value=0.031), as shown in FIG. 9, which were inversely correlated to caspase3 activation (R=−0.51, p-value=0.027).

Figure 10:
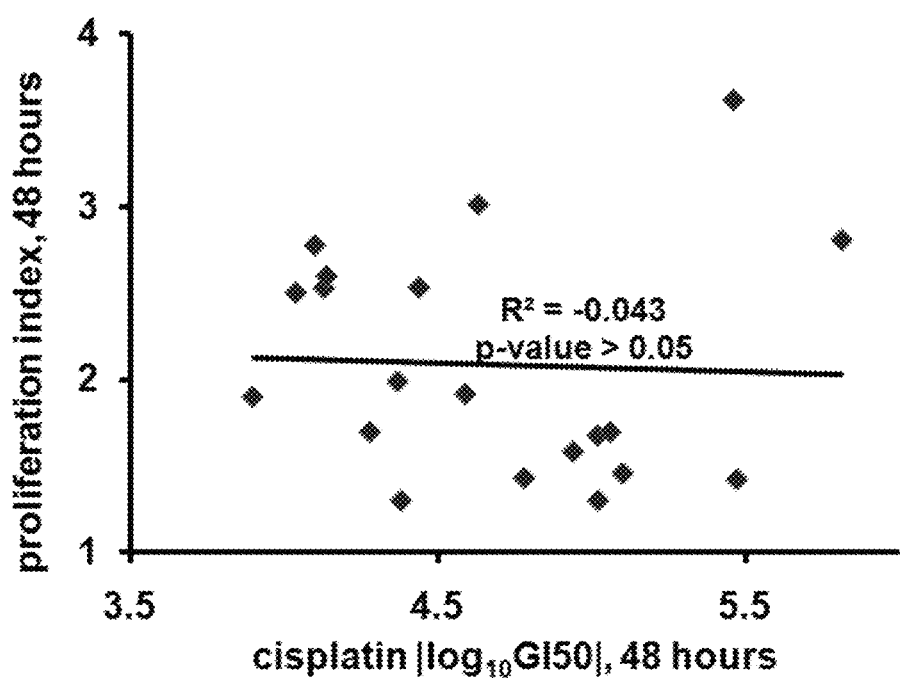
FIG. 10 shows the effect of cellular proliferation capacity on cisplatin sensitivity. It can be seen from FIG. 10 that there is no significant difference in cellular proliferation rates between cisplatin sensitive and resistant cell lines.

There was no significant difference in baseline proliferation rates between cisplatin sensitive and resistant lines as shown in FIG. 10.

Accordingly, it is evidenced that inhibition by cisplatin is significantly associated with apoptosis induction in gastric cancer and cell proliferation rate is not a good predictor of cisplatin response.

Example 2

Figure 2A:
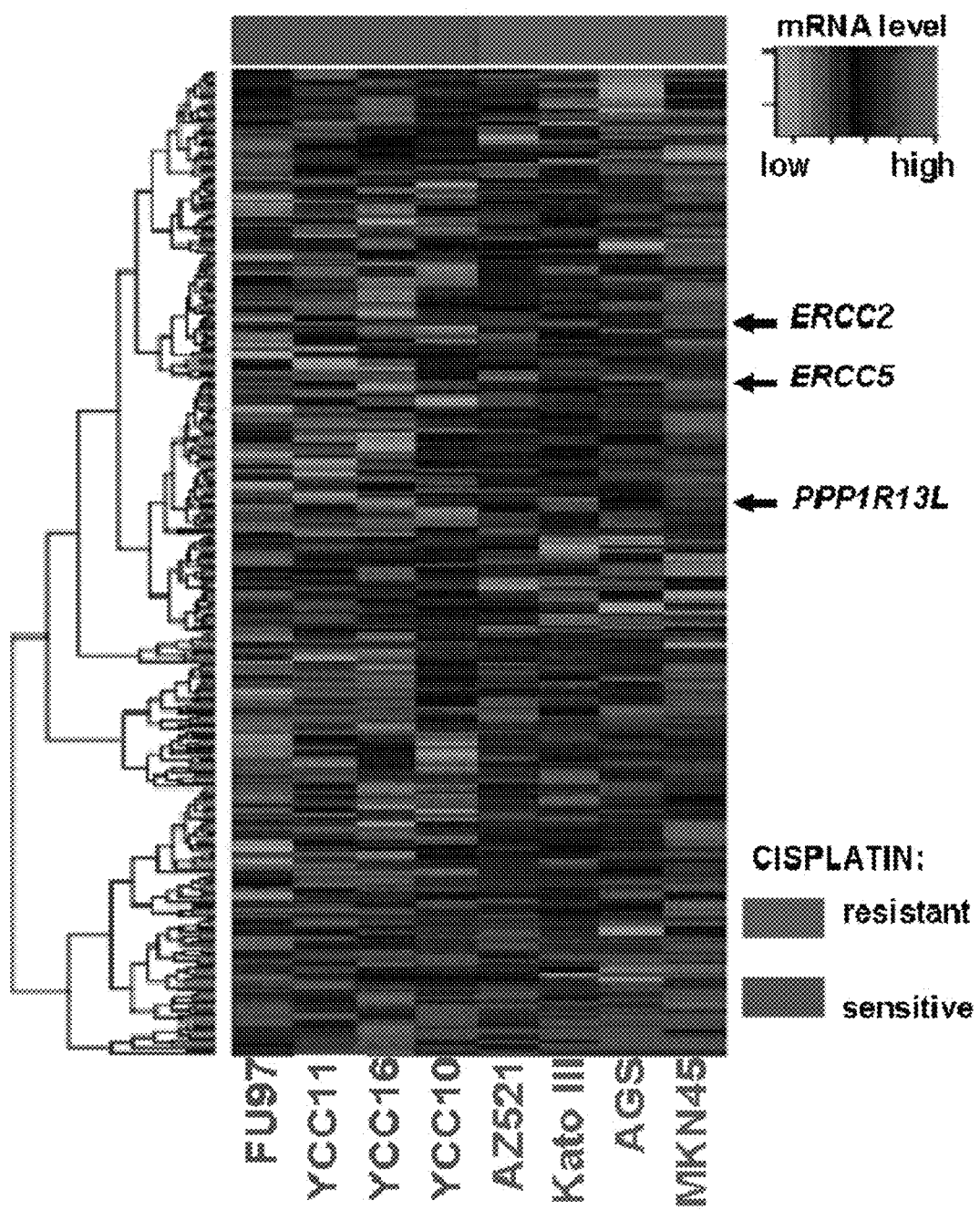
FIG. 2A shows the gene expression heat map representing genes that are differentially expressed between four cisplatin resistant and four cisplatin sensitive cell lines. Each individual row represents a gene and arrows indicate genes that were identified to mediate cisplatin resistance.

To identify candidate genes associated with cisplatin resistance, we first generated and compared gene expression profiles of the top four sensitive and resistant lines. Using the LIMMA algorithm, a modified t-test incorporating the Benjamini Hochberg multiple hypotheses correction using a p-value <0.05 significance threshold, we identified 291 differently expressed genes between sensitive and resistant lines (p-value≤0.01) as shown in FIG. 2A. Genes up-regulated in cisplatin resistant lines included ERCC2 and ERCC5, two components of the nucleotide excision repair (NER) pathway and PPP1R13L, which confer resistance to cisplatin and UV-induced apoptosis. Reciprocally, genes upregulated in the cisplatin sensitive lines were significantly associated with cellular transport processes (GO:006810, p-value=$2.13 \times 10^{-4}$).

Bona-fide cisplatin resistance genes were nominated from the identified several hundred (~300) exhibiting differential expression patterns between sensitive and resistant lines with the integration of the additional molecular criteria of DNA methylation. GoldenGate Methylation arrays, were used to quantify CpG methylation levels at 1505 CpG sites corresponding to 807 genes across the lines. On the methylation array, CpG probes are named relative to the transcription start site of a gene. For example, probe MGMT P281 refers to a CpG probe −281 bp from the MGMT transcription start site. Variable methylation of several genes previously reported as methylated in GC, including MGMT (YCC10, TMK1, Hs746T), MLH1 (IM95), and APC (all cell lines except AZ521 and Hs746T) were observed.

Figure 11A:
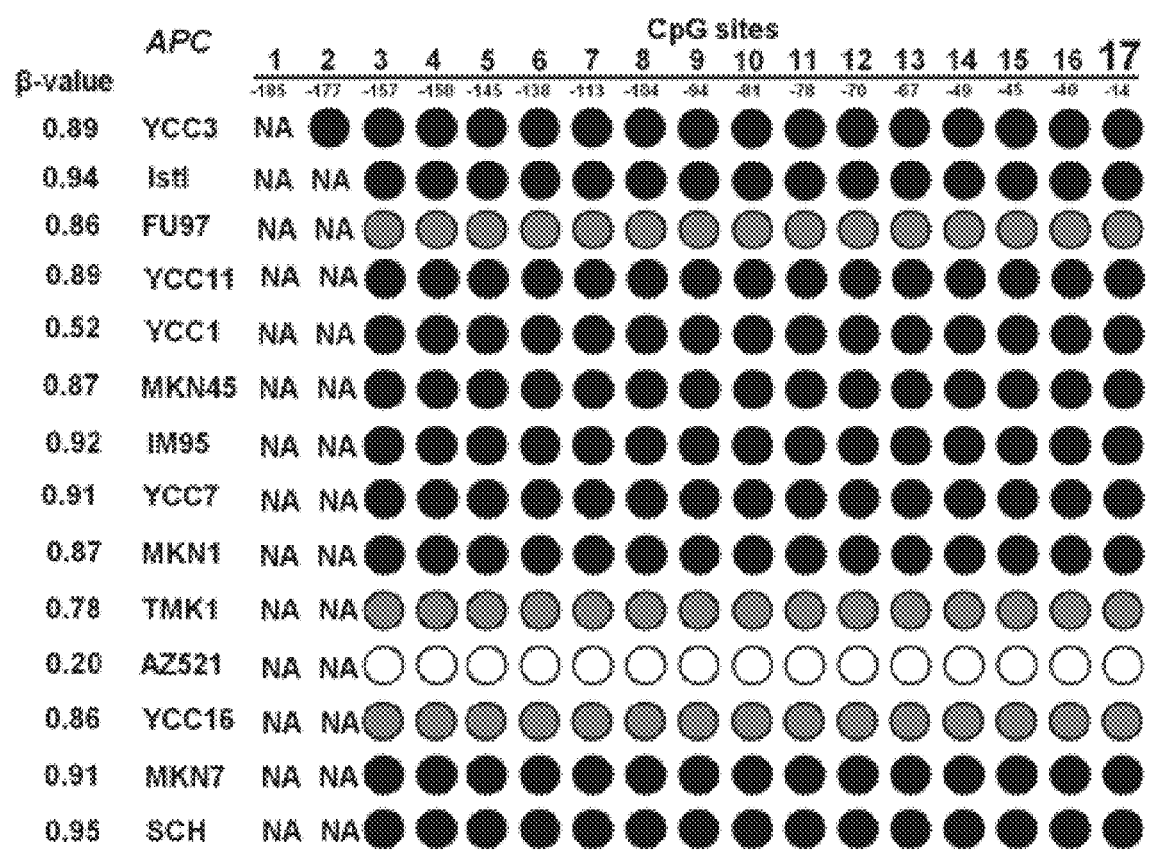
Figure 11B:
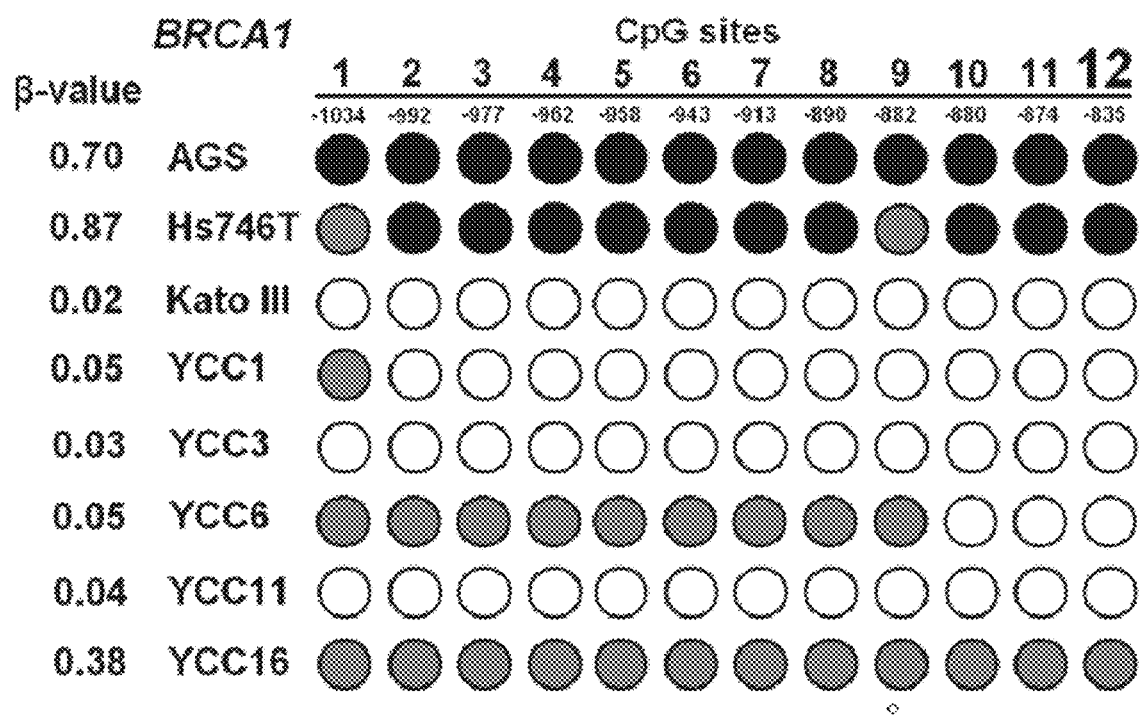

The GoldenGate platform results were validated with bisulfite sequencing analysis on three genes exhibiting variable cell line methylation—APC (P14), BRCA1 (P835) and S100A2 (P1186). The results as shown in FIG. 11 confirmed that CpG probes with β-values >0.2 were consistently associated with increased DNA methylation.

Accordingly, these results confirm the technical validity of the GoldenGate methylation data.

Figure 12:
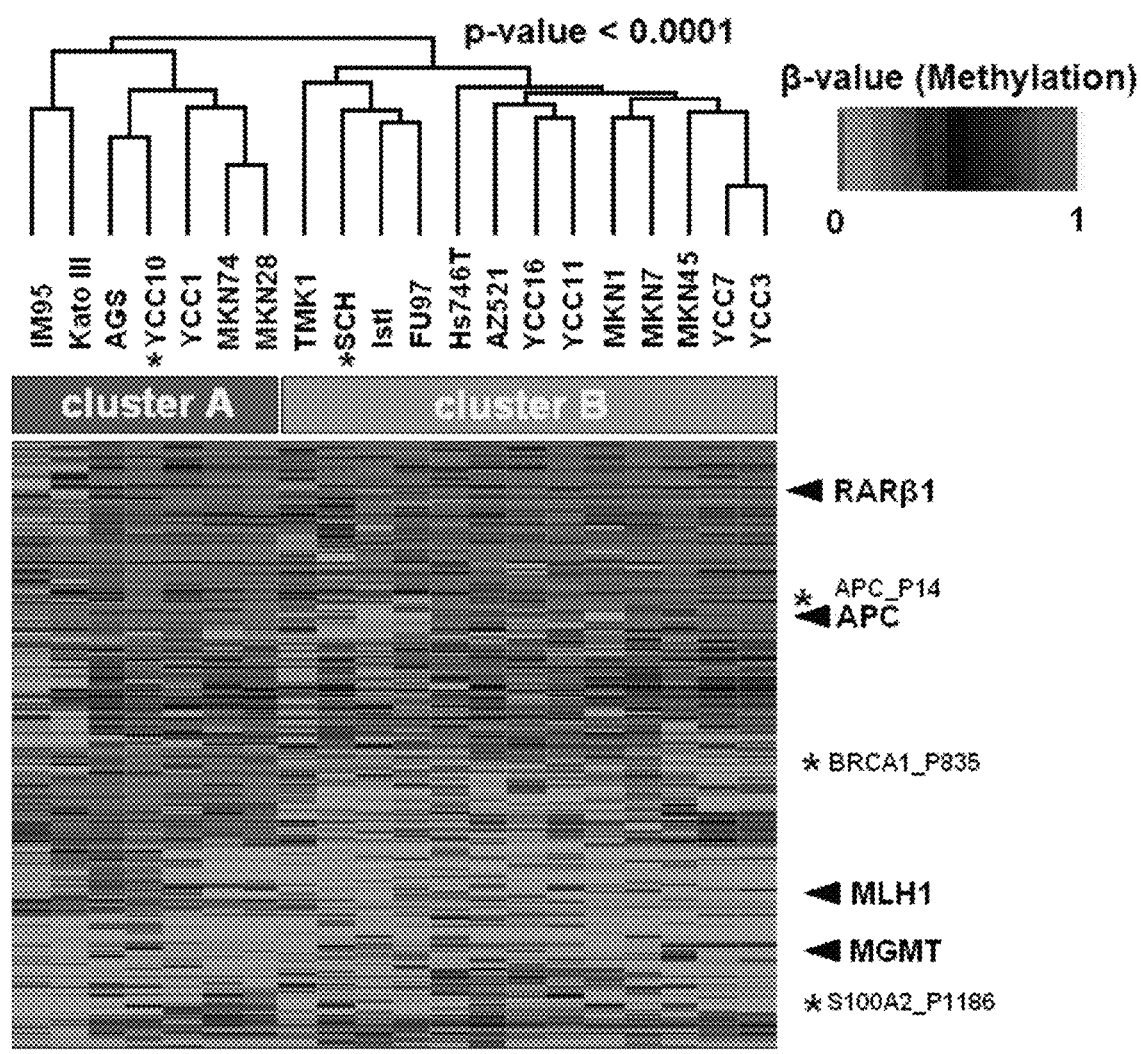
FIG. 12 shows the global DNA methylation pattern of 20 gastric cancer cell lines. The heat map depicts methylation status of 20 gastric cancer cell lines arranged by hierarchical clustering of cell lines and DNA methylation scores represent by β-value for each gene probe.

Interestingly, unsupervised clustering analysis identified two major cell line clusters, with one cluster exhibiting an overall higher level of global methylation than the other (p-value<0.0001) as seen in FIG. 12.

Accordingly, this result demonstrates that some GCs exhibit "hypermethylation".

Figure 2B:
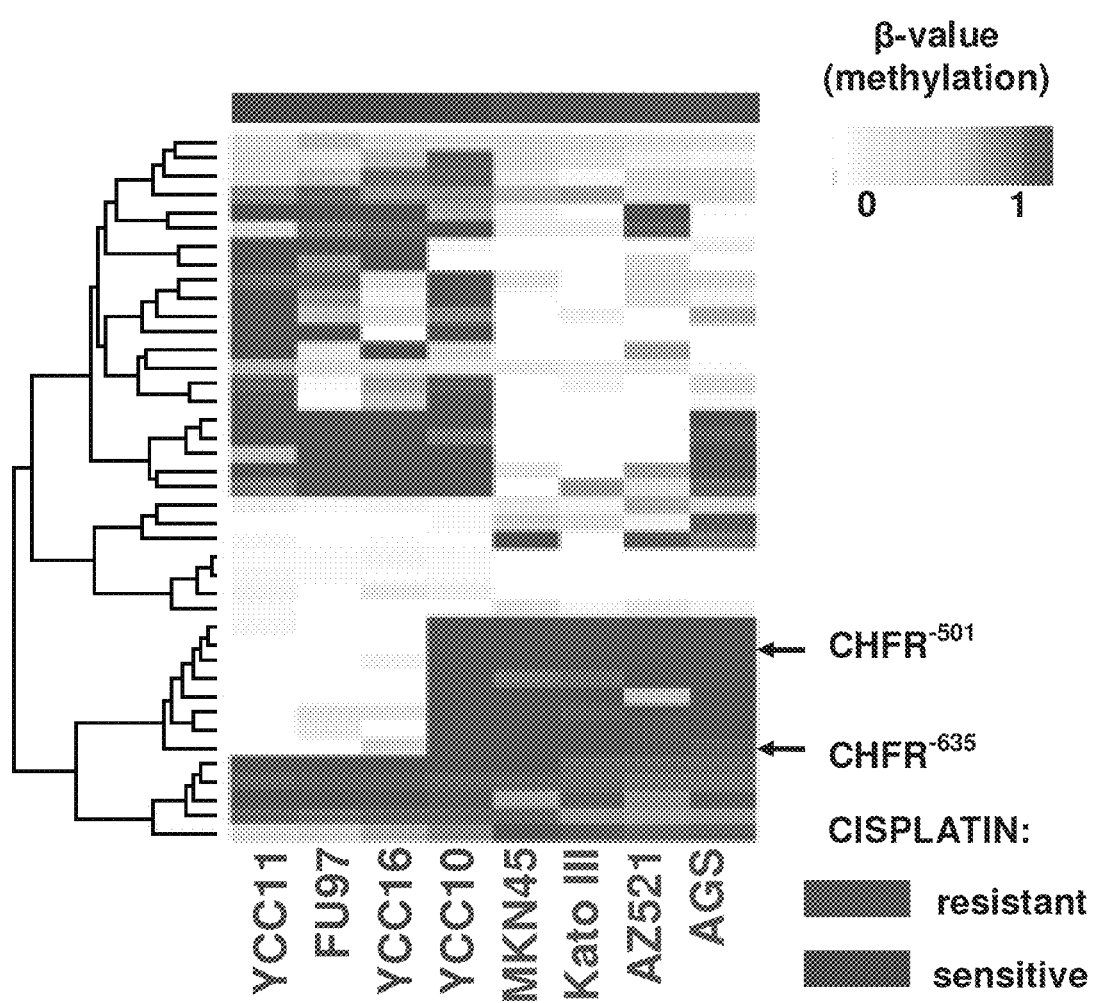
FIG. 2B shows the DNA methylation heat map representing differentially methylated CpG sites between four cisplatin sensitive and four resistant cell lines. Each row represents a distinct CpG probe and the arrows highlight probes associated with the CHFR gene previously implicated in chemotherapy response in gastric cancer.

Using LIMMA, CpG probes differentially methylated between the top four cisplatin sensitive lines (YCC10, YCC16, YCC11, FU97) and the top four resistant lines (AGS, MKN45, AZ521, Kato III) were identified. 41 CpG probes were differently methylated between the 2 groups, corresponding to 37 genes (p-value≤0.05 after multiple hypothesis correction), as shown in FIG. 2B. 27 probes (66%) were associated with CpG islands in promoter proximal regions, while the remaining 14 probes were associated with non-CpG island regions. Two CpG probes exhibiting increased methylation in cisplatin resistant lines were associated with CHFR, a gene associated with microtubule inhibitor response in GC.

TABLE 2

Genes associated with both gene expression and DNA methylation differences between sensitive and resistant lines.

| Gene name | Gene annotation | DNA methylation status in sensitive lines | mRNA expression status in sensitive lines |
| --- | --- | --- | --- |
| TFPI2 | Tissue factor pathway inhibitor 2 | Unmethylated | Up |
| BMP4 | Bone morphogenetic protein 4 | Methylated | Down |
| CD9 | CD9 antigen (p24) | Methylated | Down |
| DSC2 | Desmocollin 2 | Methylated | Down |
| CDH17 | Cadherin 17, LI cadherin (liver-intestine) | Methylated | Down |

Figure 2C:
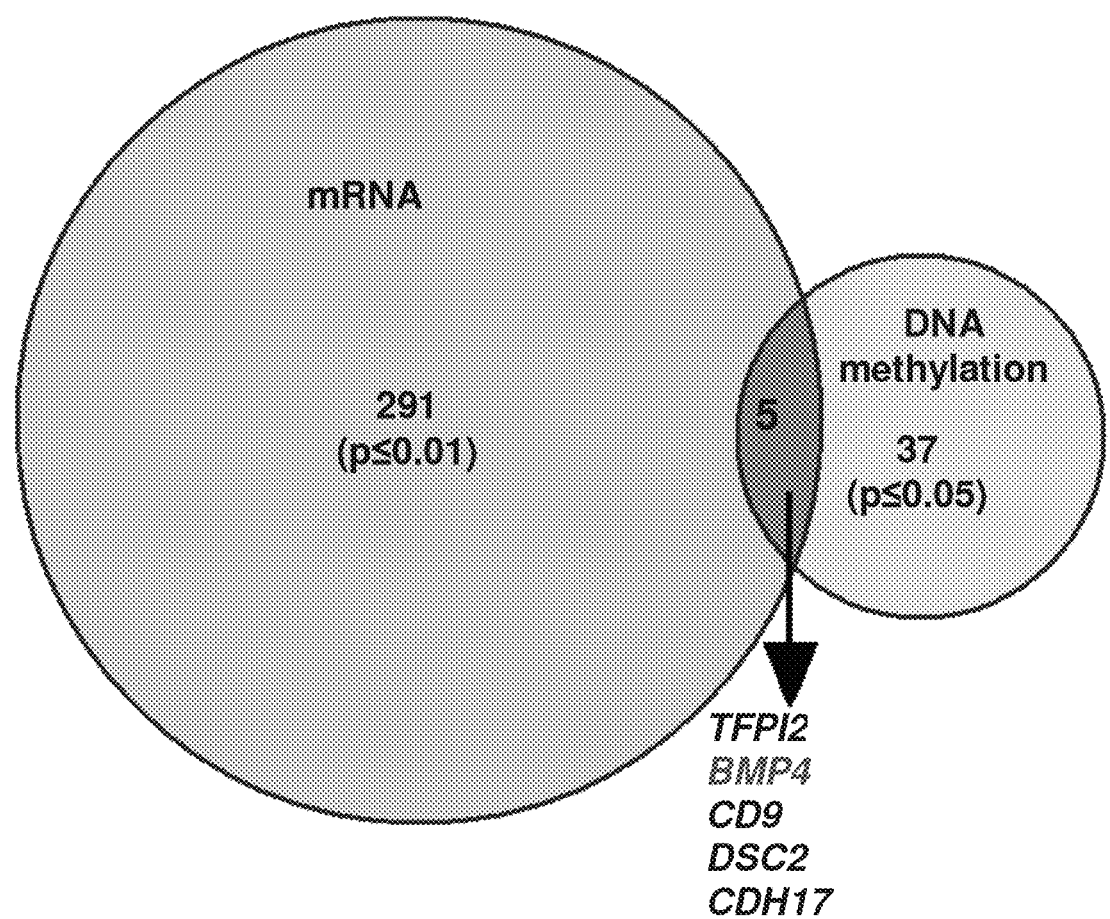
FIG. 2C shows the Venn diagram of the gene overlap between the transcriptomic and epigenetic signatures. 5 genes are found in the intersect of the Venn diagram of which one is BMP4.

The companion lists of differentially expressed and differentially methylated genes were intersected. The results identified five genes that were both differently methylated and differentially expressed between the cisplatin-sensitive and resistant groups (BMP4, CD9, DSC2, CDH17, and TFPI2) as shown in FIG. 2C and Table 2.

Figure 13A:
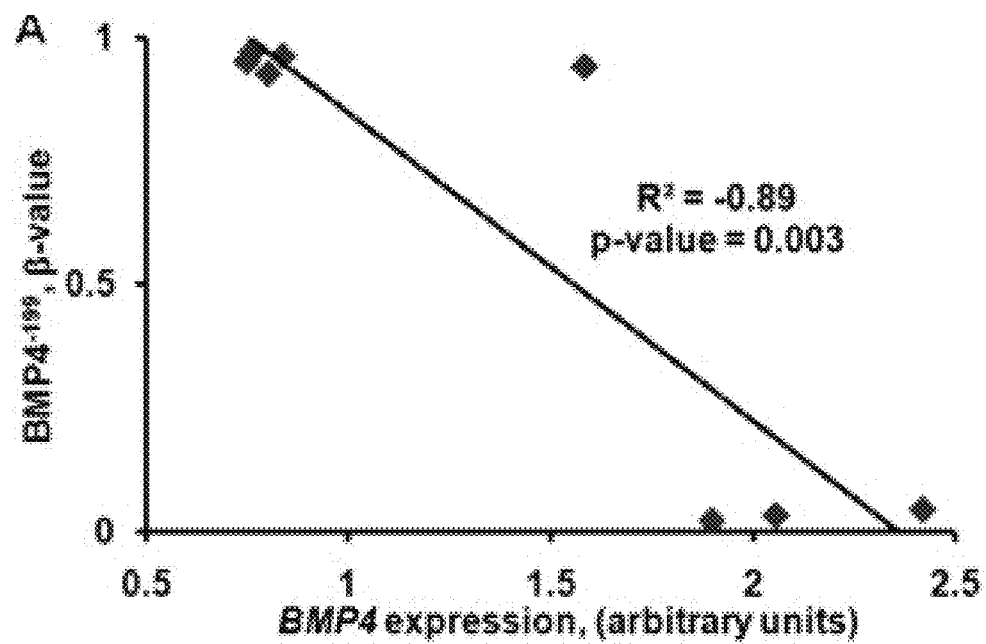
FIG. 13A to 13B shows the effect of BMP4 methylation on BMP4 mRNA expression. It can be seen from FIG. 13A that 13B that BMP4 methylation is inversely correlated to BMP4 expression.
Figure 13A:
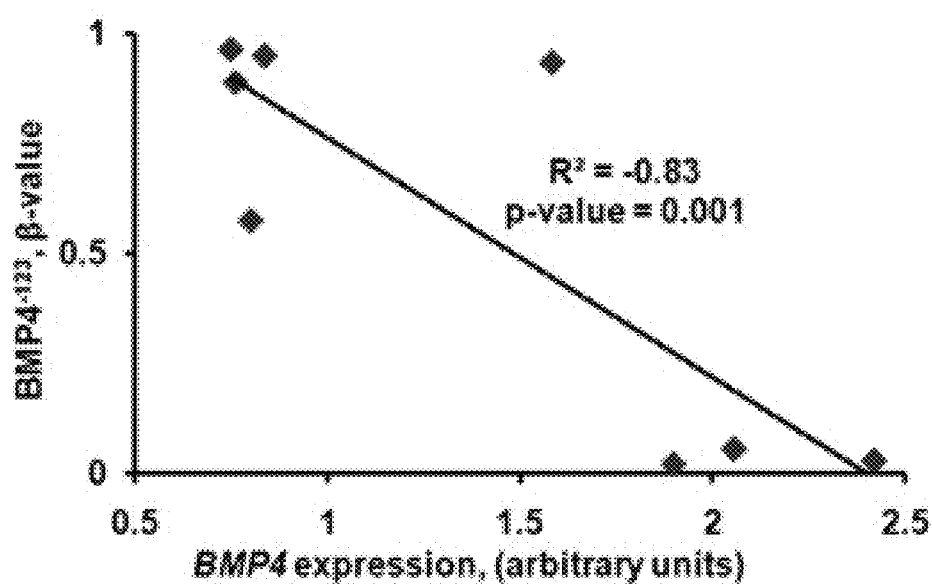
Figure 13B:
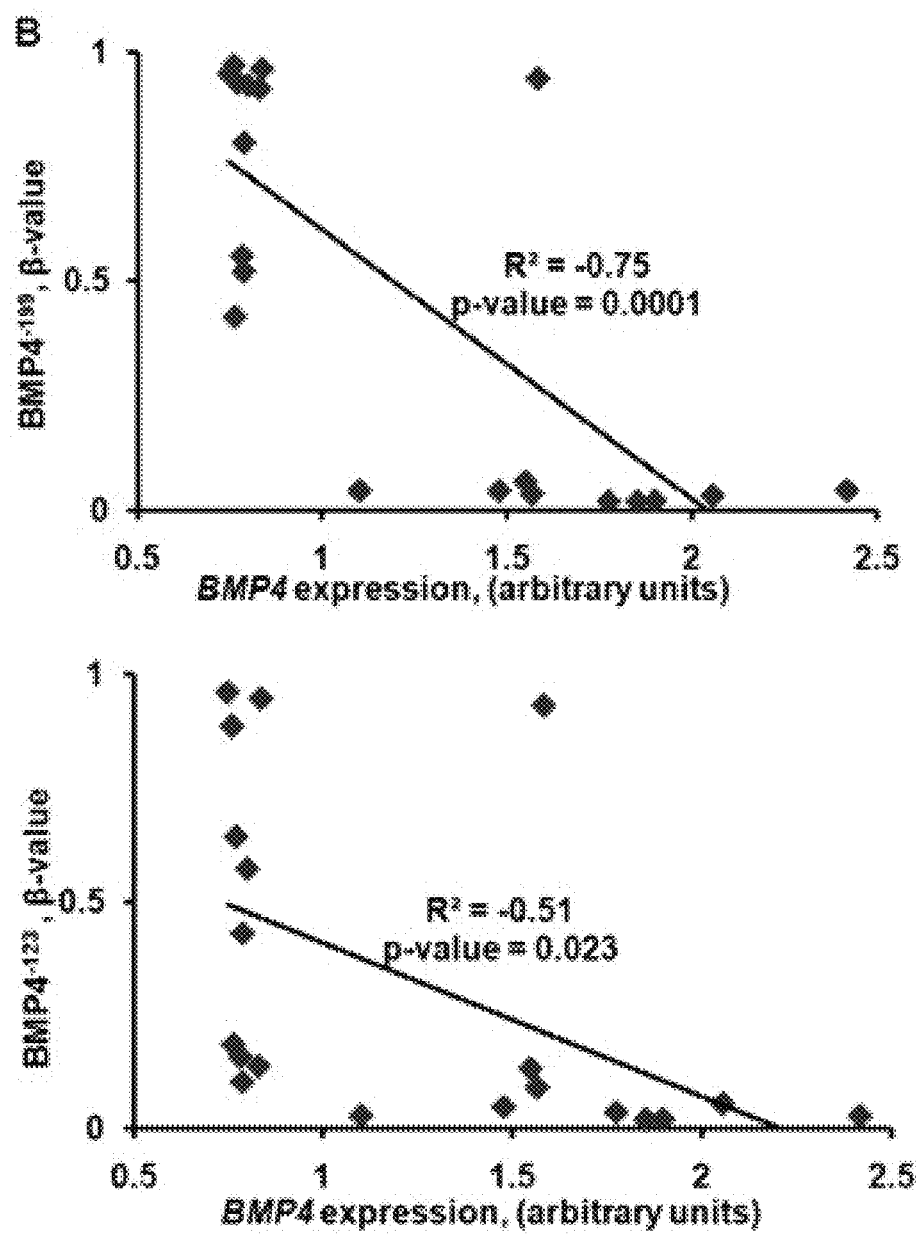
Figure 13C:
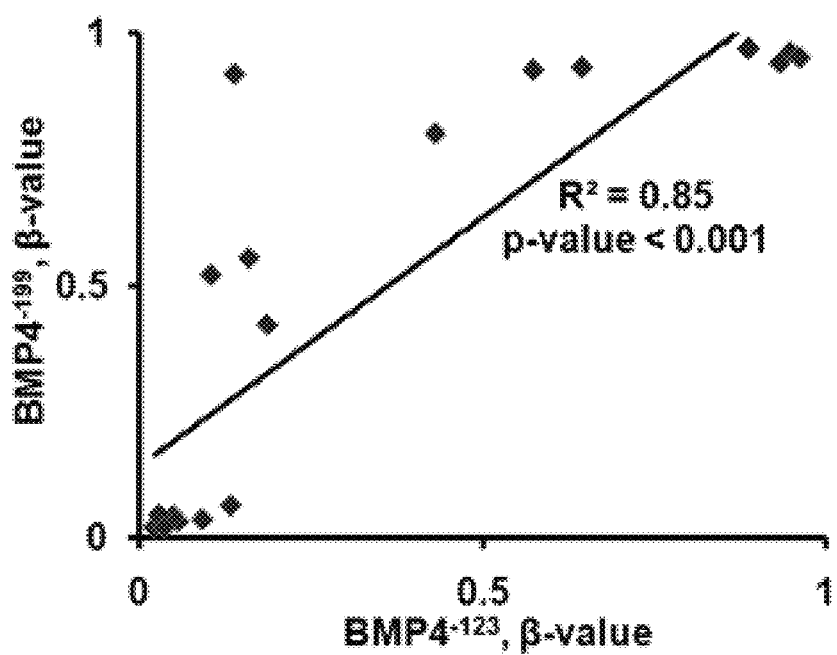
FIG. 13C shows that BMP4$^{-199}$ and BMP4$^{-123}$ methylation are significantly correlated to one another.
Figure 14:
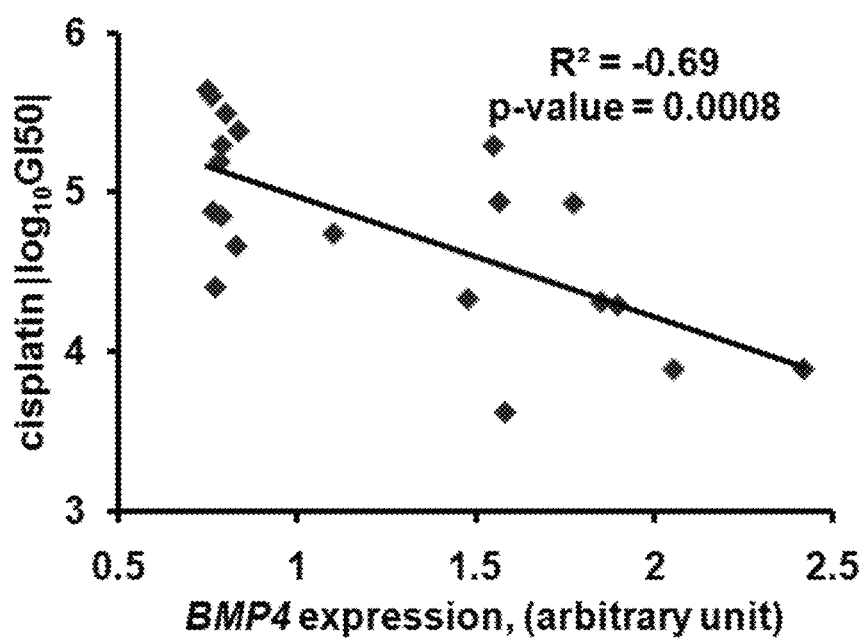
FIG. 14 shows the association of BMP4 mRNA expression with cisplatin sensitivity. It can be seen from FIG. 14 that BMP4 mRNA expression is associated with cisplatin sensitivity.
Figure 15A:
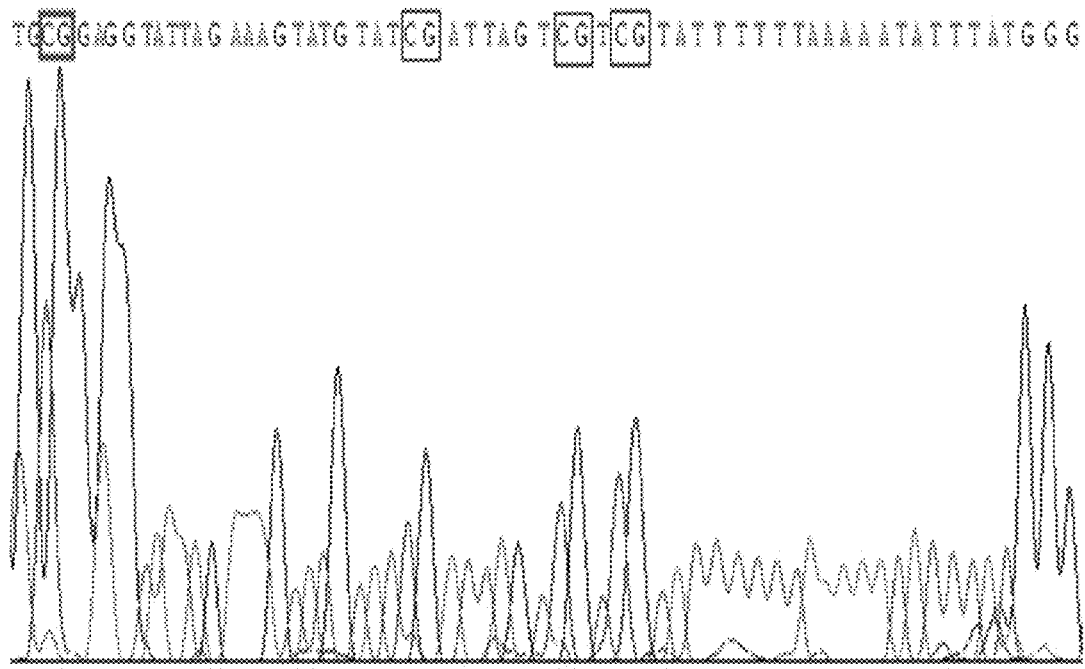
FIG. 15A to 15G show the results of bisulfite sequencing of the BMP4$^{-199}$ probe region in four cisplatin sensitive (YCC10, YCC16, YCC11, FU97) and three cisplatin resistant cell lines (MKN45, AZ521, KatoIII). From FIG. 15, it can be seen that all CpG sites within the region were fully methylated in cisplatin sensitive lines but unmethylated in resistant lines.
Figure 15B:
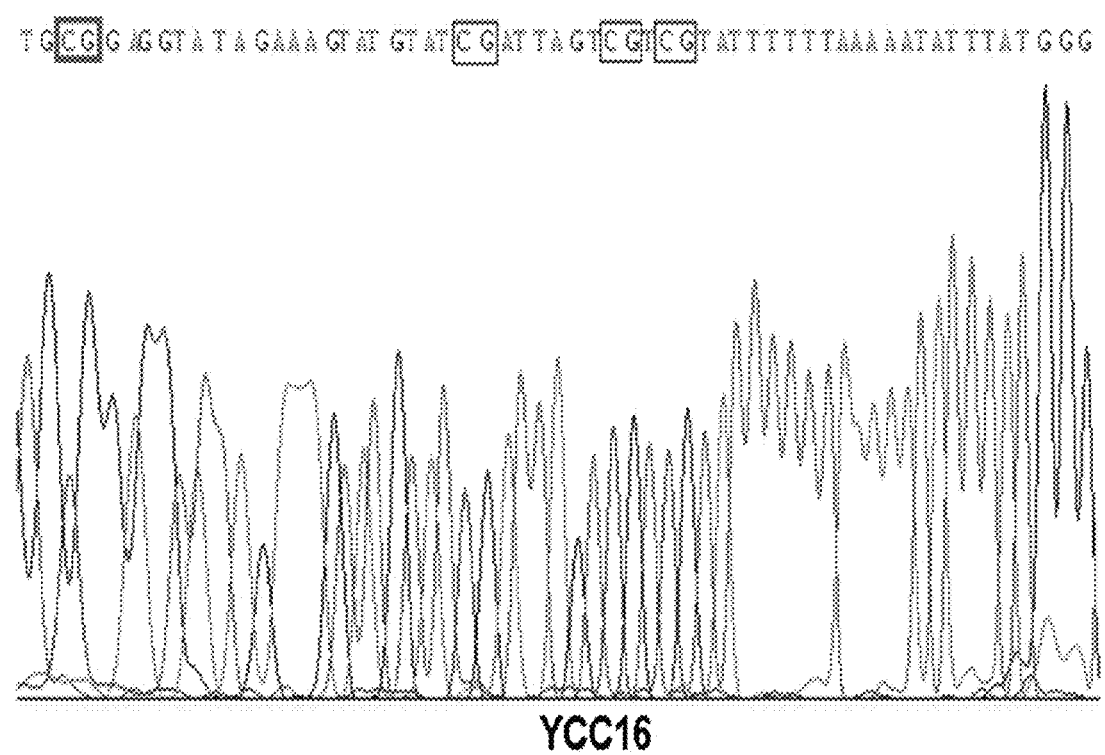
Figure 15C:
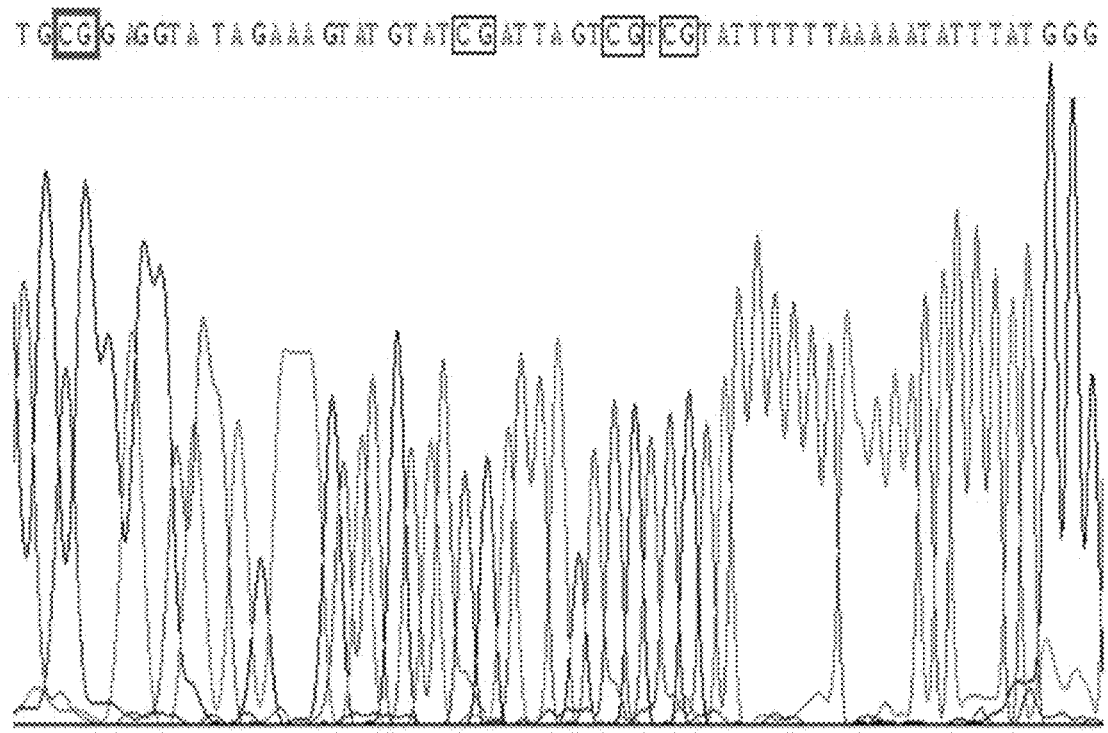
Figure 15D:
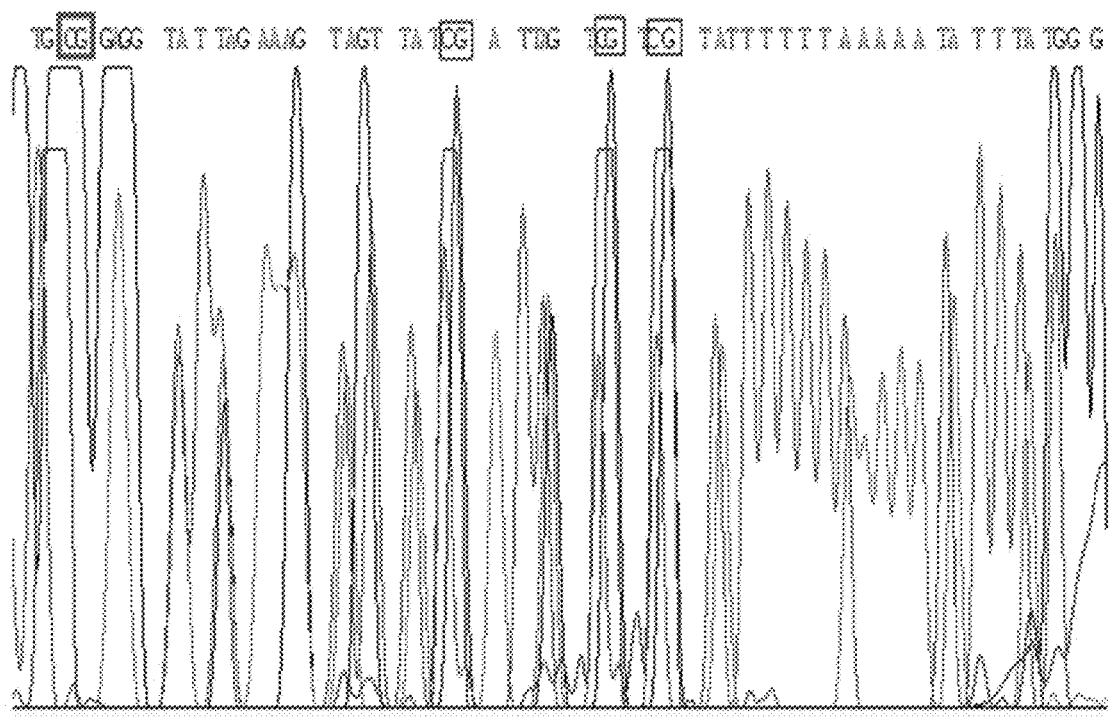
Figure 15E:
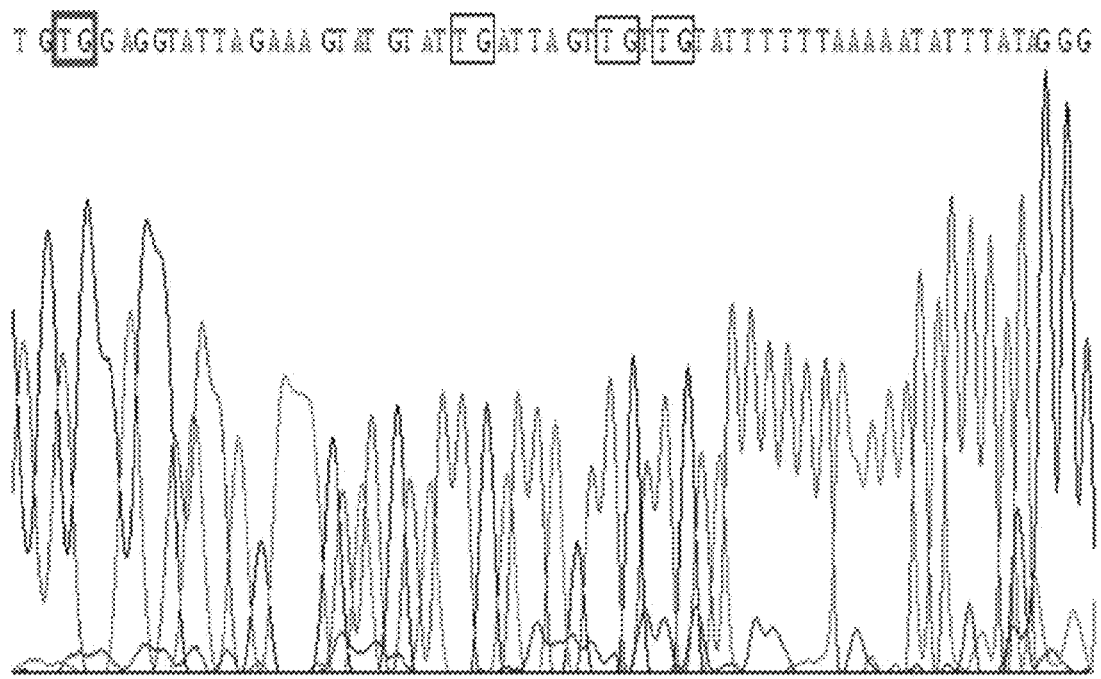
Figure 15F:
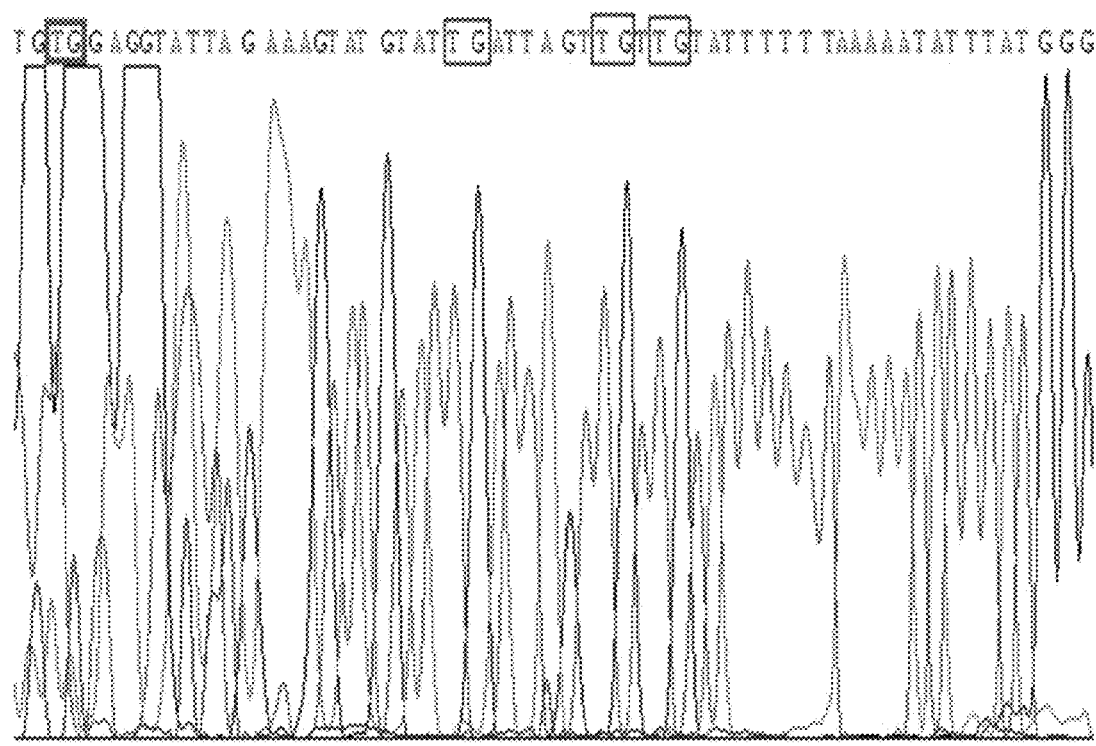
Figure 15G:
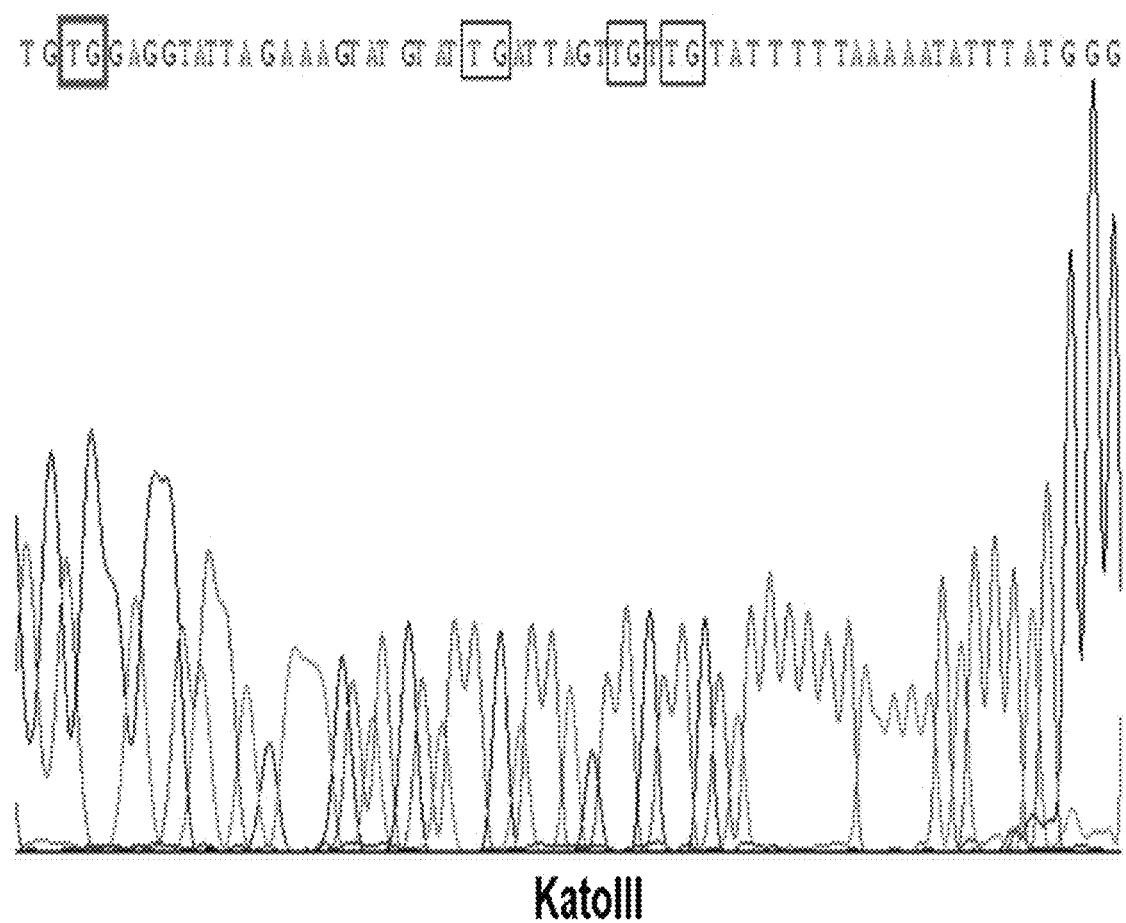

One of these genes—BMP4, a member of the bone morphogenetic protein family, was picked for further characterization. As seen in FIG. 13A, BMP4 methylation at CpG sites −199 (BMP4$^{-199}$) and −123 (BMP4$^{-123}$), both lying in the CpG island, were inversely correlated with BMP4 expression in the initial panel of 8 sensitive and resistant lines (p-value=0.003, p-value=0.01) and also across the 20 cell line panel (p-value=0.0001, p-value=0.023). BMP4$^{-199}$ and BMP4$^{-123}$ methylation were significantly correlated to one another (p-value <0.001), however BMP4$^{-199}$ methylation exhibited a stronger correlation with BMP4 gene expression than the BMP4$^{-123}$ site. Both BMP4$^{-199}$ and BMP4$^{-123}$ methylation were inversely correlated with cisplatin resistance in the GC lines (p-value<0.05 for both sites), while BMP4 expression levels were positively correlated with cisplatin resistance (p-value=0.0008) as seen in FIG. 14.

Example 3

This example demonstrates the confirmation of BMP4 as a differentially methylated gene.

Figure 3A:
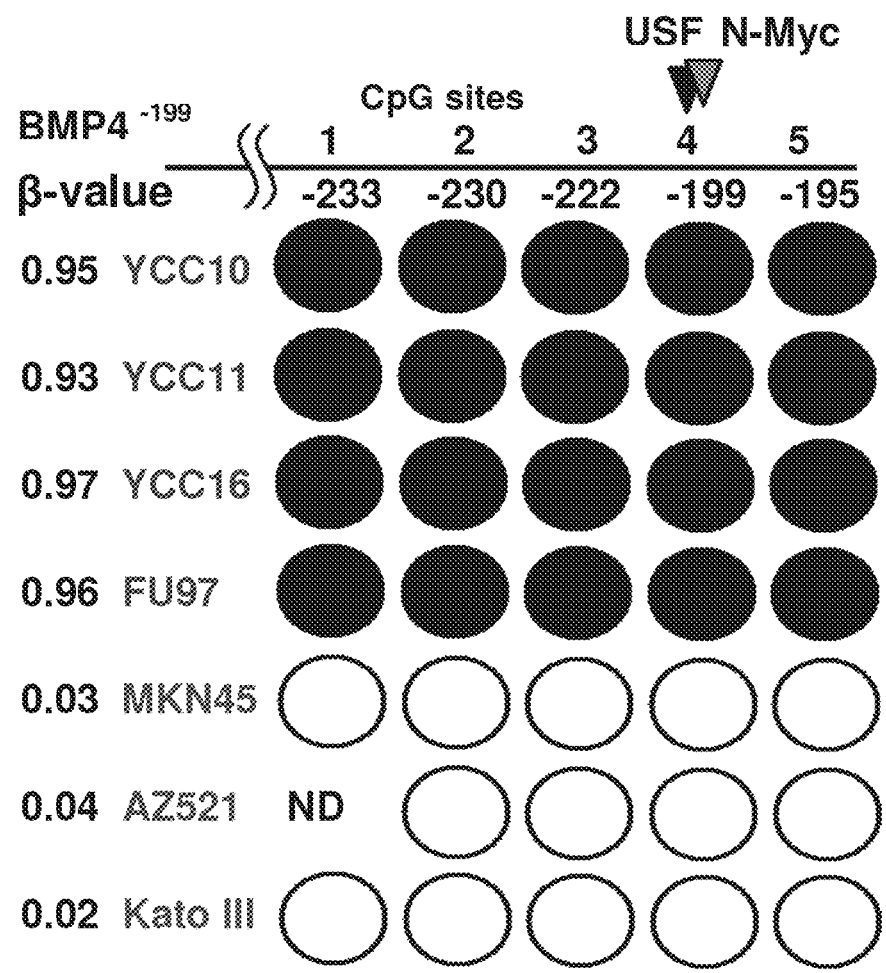
FIG. 3A shows the bisulphite sequencing analysis of the BMP4$^{-198}$ CpG island ($^{-198}$ refers to the position within the BMP4 gene relative to the transcription start site) in four cisplatin-sensitive (YCC10, YCC11, YCC16, FU97) and three cisplatin-resistant (MKN45, AZ521, Kato III) cell lines. Each circle represents a CpG site within the CpG island numbered relative to the transcriptional start site. Black circles represent sites that are fully methylated and white circles represent sites that are fully unmethylated. From FIG. 3A, it can be seen that CpG sites are fully methylated in cisplatin-sensitive cell lines and fully unmethylated in cisplatin-resistant cell lines.
Figure 3B:
FIG. 3B shows the methyl-specific PCR analysis of the BMP4$^{-123}$ CpG site for four cisplatin-sensitive and three cisplatin resistant cell lines using primers recognizing the methylated (M) or unmethylated (U) sequences. Methylation array β-values for the BMP4$^{-123}$ CpG probes are shown in the bottom row. It can be seen from FIG. 3B that BMP4 is methylated in cisplatin-sensitive cell lines and unmethylated in cisplatin-resistant cell lines.

Targeted methylation analysis of the BMP4 gene promoter in cisplatin sensitive and resistant lines was performed to confirm BMP4 as a differentially methylated gene. Bisulfite sequencing of the BMP4$^{-199}$ region confirmed that all five CpG sites within the region were fully methylated in cisplatin sensitive lines (YCC10, YCC11, YCC16, FU97) but unmethylated in resistant lines (MKN45, AZ521, Kato III) as shown in FIGS. 3A and 15. Similarly, methyl-specific PCR (MS-PCR) analysis of the BMP4$^{-123}$ confirmed BMP4 methylation in cisplatin sensitive lines (YCC10, FU97, YCC11, YCC16) but not in resistant lines (MKN45, AZ521, Kato III) as shown in FIG. 3B.

Gastric cancer cell lines were treated with 5-aza-2'-deoxycytidine (5-azadC), a chemical inhibitor of DNA methyltransferases to investigate if BMP4 gene expression is regulated by BMP4 promoter methylation.

Figure 3C:
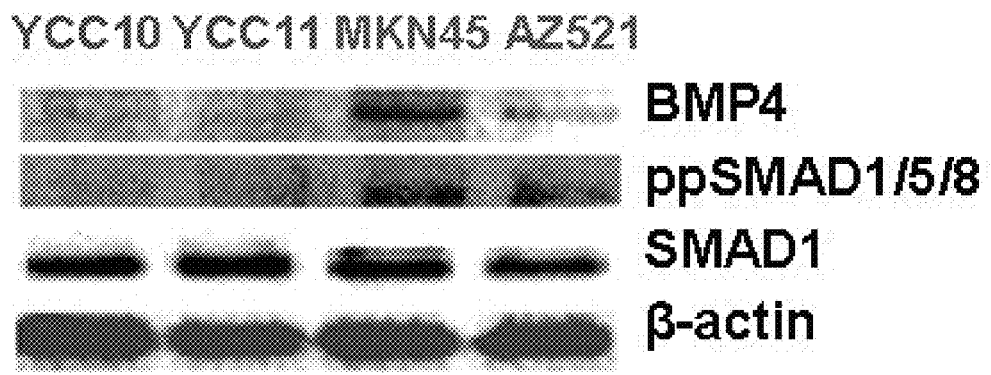
FIG. 3C shows BMP4 expression and BMP pathway status in cisplatin-sensitive and resistant cell lines. It can be seen from FIG. 3C that BMP4 protein and ppSMAD1/5/8 is expressed in cisplatin-resistant but not sensitive cell lines.
Figure 3D:
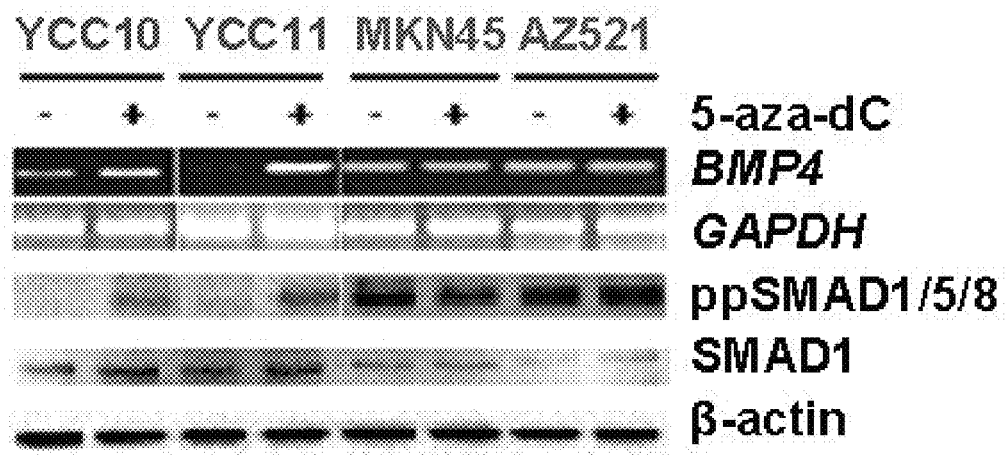
FIG. 3D shows BMP4 expression before and after treatment with demethylating agents. From FIG. 3D, it can be seen that in cisplatin-sensitive cell lines, BMP4 expression is upregulated and phosphorylation of BMP pathway targets is increased after treatment with the demethylating agent.

The results presented in FIG. 3D demonstrate that in cisplatin sensitive lines YCC10 and YCC11 where the BMP4 promoter is methylated, BMP4 transcripts were up-regulated after 5-azadC treatment. Supporting the biological relevance of this BMP4 upregulation, increased phosphorylation of the BMP-downstream targets SMAD1/5/8 after 5-azadC treatment was also observed. In contrast, 5-azadC treatment did not alter BMP4 expression in the resistant cell lines MKN45 and AZ521 where the BMP4 promoter is unmethylated and BMP4 is already highly expressed. The cisplatin resistant lines (MKN45 and AZ521) also exhibited constitutive activation of BMP signaling as measured by phosphorylated SMAD1/5/8, which was not affected by 5-azadC treatment as seen in FIG. 3C.

These results demonstrate that BMP4 promoter methylation regulates BMP4 expression, and that the high levels of BMP4 expression in cisplatin resistant lines cause activation of downstream components in the canonical BMP signaling pathway.

Example 4

This example demonstrates the investigation of the role of BMP4 as a pro- or anti-oncogenic role in gastric cancer. BMP4 expression in different GC cell lines were genetically manipulated and their resultant phenotypes were studied.

The results show that stable silencing of BMP4 in AZ521 cells (a cisplatin resistant line) by BMP4 shRNAs caused inhibition of BMP4 pathway signaling, indicated by decreased phosphorylation of SMAD1/5/8. Similar results were obtained using an independent non-overlapping BMP4 shRNA, indicating that this phenotype is specific to BMP4 and not an off-target effect, as seen in the left panel of FIG. 4A.

Figure 4A:
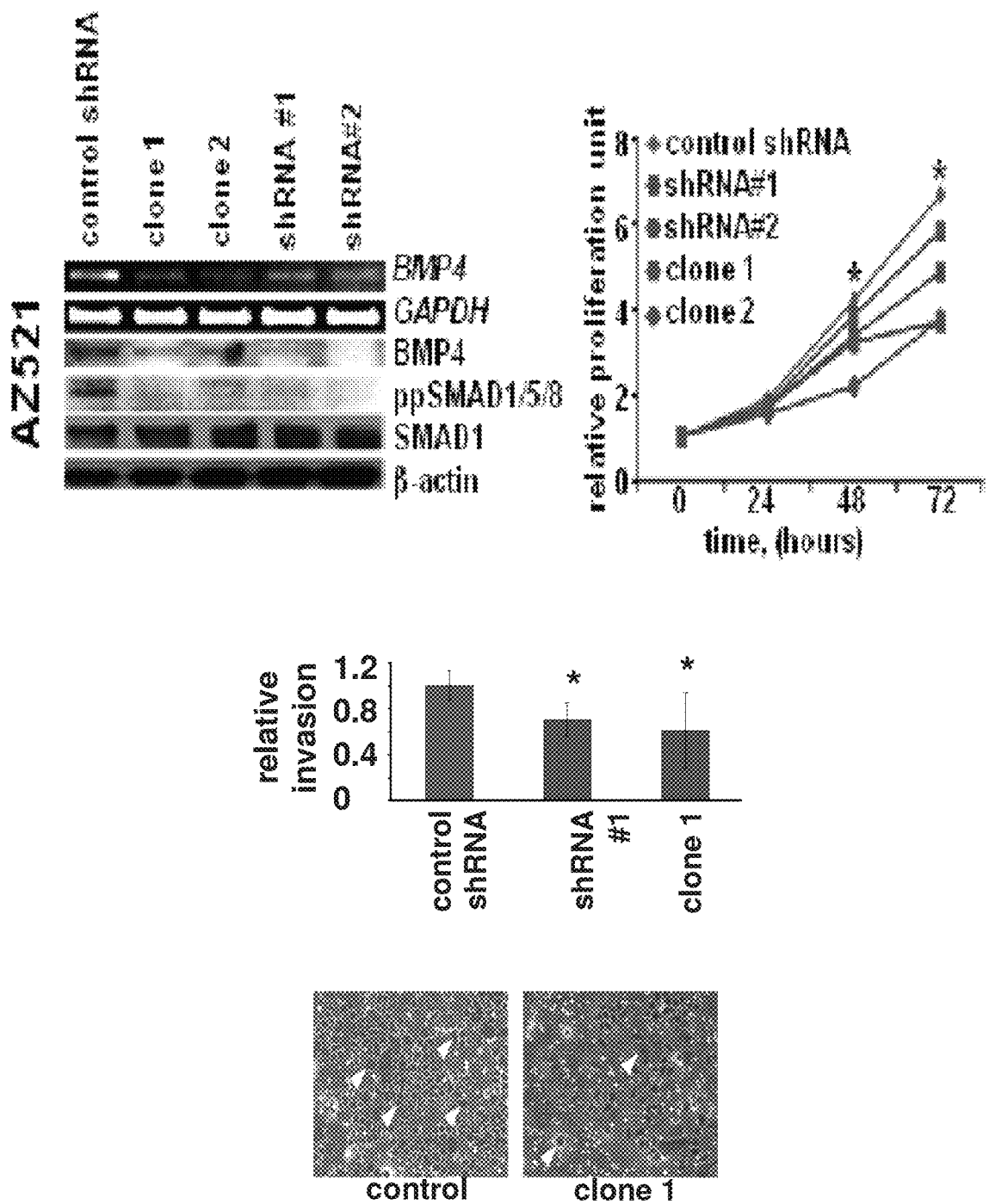
FIGS. 4A and 4B show the effect of silencing and overexpressing BMP4 on cisplatin resistant and sensitive cell lines respectively. From FIG. 4A it can be seen that BMP4 silencing leads to decreased phosphorylation of SMAD1/5/8 and reduced cellular proliferation and migration while the opposite effect can be seen by BMP4 overexpression in FIG. 4B.
Figure 4B:
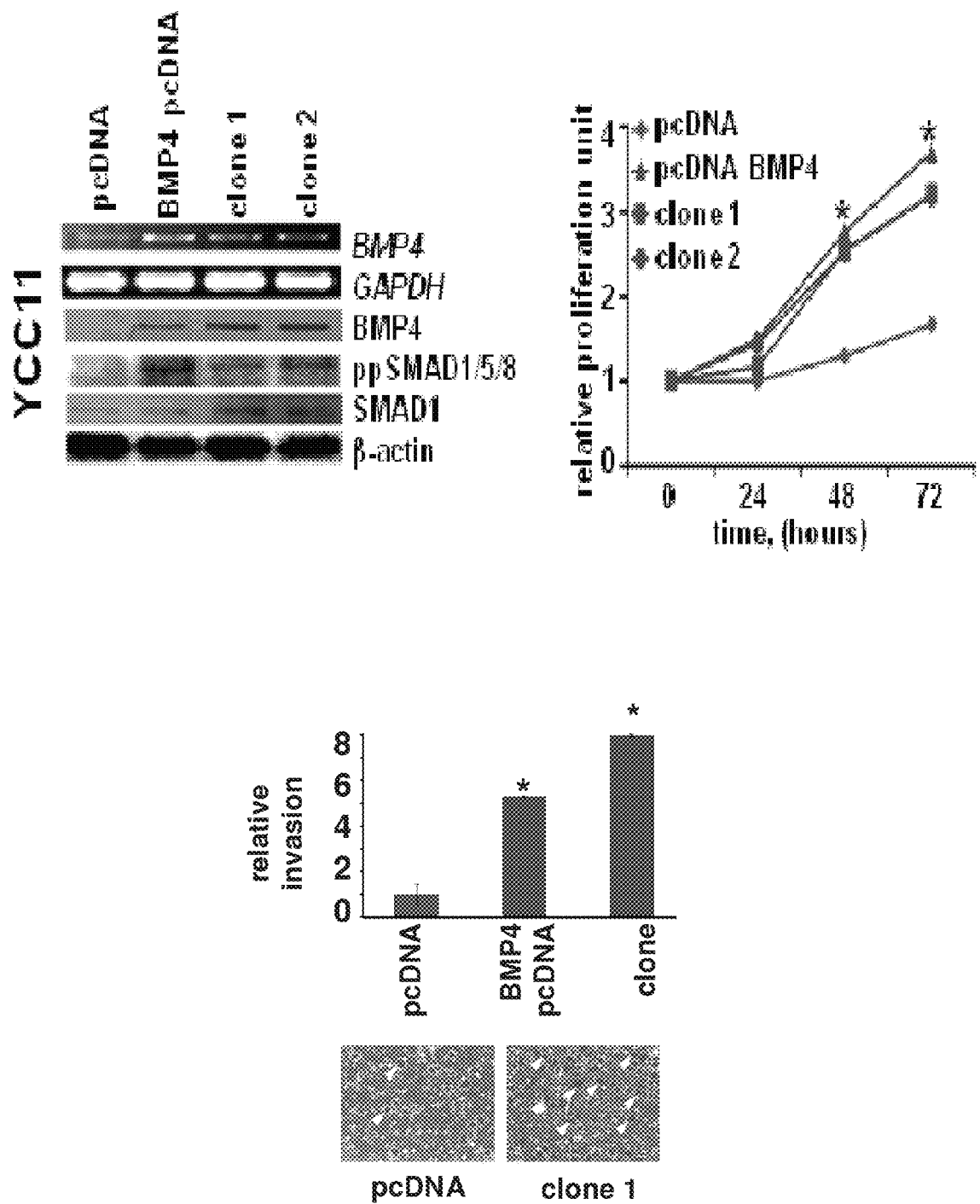

BMP4-silenced AZ521 cells exhibited a significant inhibition of cellular proliferation (p-value≤0.01) as seen in the right panel of FIG. 4A and also reduced cellular migration in a Matrigel invasion assay (p<0.05) as seen in the bottom panel of FIG. 4A. In the reciprocal experiment, BMP4 was stably over-expressed in YCC11 cisplatin sensitive cells. BMP4 over-expressing YCC11 cells exhibited constitutive phosphorylation of SMAD1/5/8 as shown in the left panel of FIG. 4B, and also significantly higher cell proliferation and invasion rates than parental control cells as seen in the right and bottom panels of FIG. 4B (p-value<0.01 for proliferation and p-value<0.05 for invasion).

This result demonstrates that BMP4 plays a pro-oncogenic role in GC, as BMP4 silencing suppresses cell proliferation/invasion while BMP4 overexpression can enhances these traits.

Figure 4C:
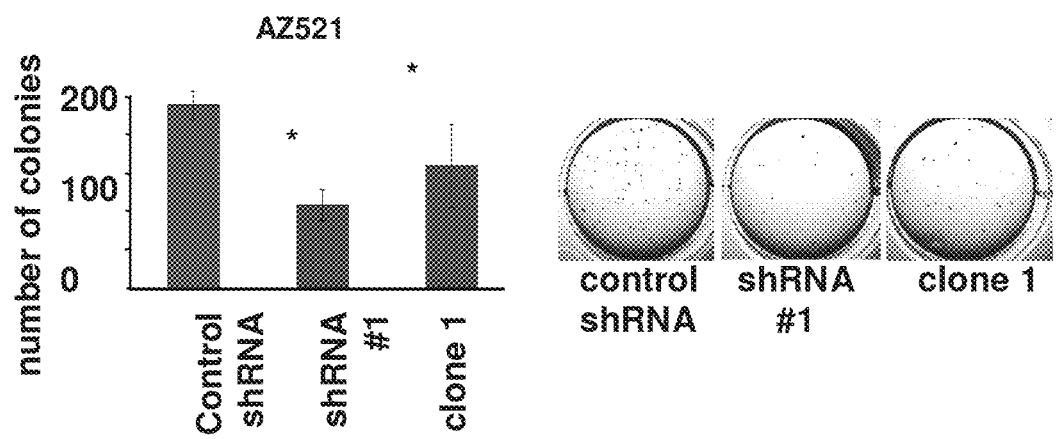
FIG. 4C shows the effect of BMP4 silencing on tumorigenesis in vitro and in vivo where soft agar colony formation and tumor burden is reduced respectively.
Figure 4C:
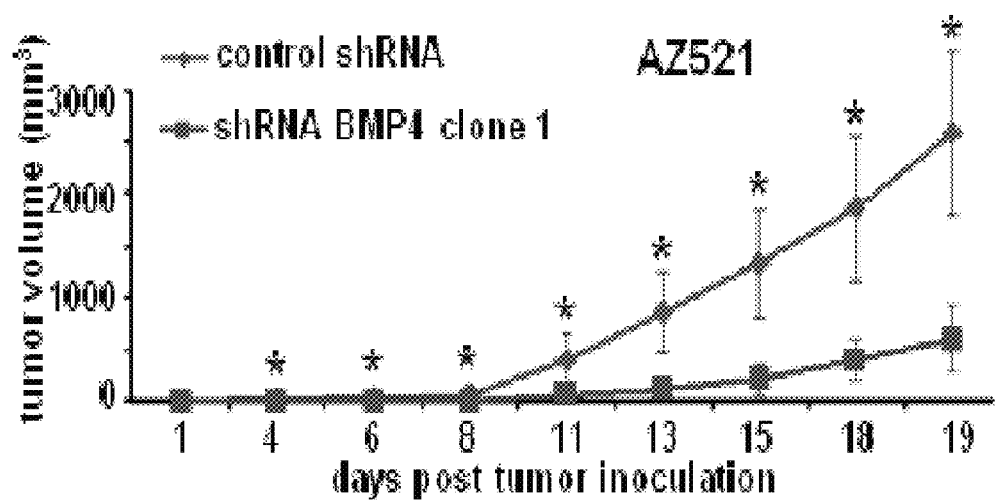

In a soft-agar colony formation assay, BMP4-silenced AZ521 cells exhibited significantly decreased anchorage-independent growth compared to control AZ521 cells as seen in the top panel of FIG. 4C (p-value<0.05). Similarly, in a murine xenograft flank assays, where cells are injected into the right flank of the animals, BMP4-silenced AZ521 cells developed flank tumors in nude mice that were significantly smaller in size (day 20: 600 mm$^3$ vs 2598 mm$^3$, p-value=0.003) and at a slower rate that parental AZ521 cells as shown in the bottom panel of FIG. 4C.

These results taken collectively, indicate that BMP4 expression enhances multiple pro-oncogenic traits in GC.

Example 5

Figure 5A:
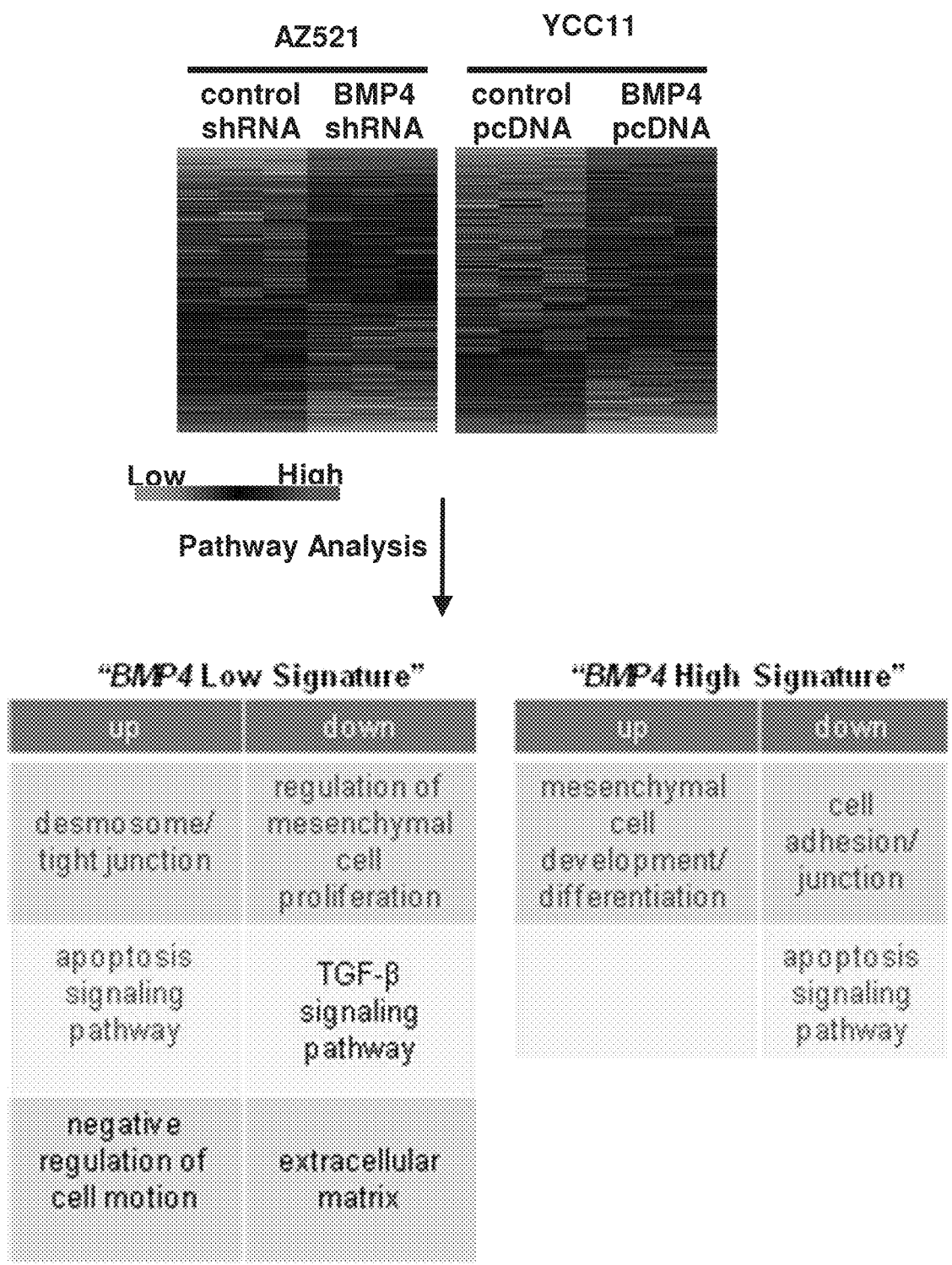
FIG. 5A shows heat maps of gene expression signature associated with BMP4 silencing or BMP4 overexpression. Both BMP4 Low' and BMP4 High' expression signatures were subjected to pathway analysis. It can be seen from FIG. 5A that genes related to mesenchymal development are downregulated after BMP4 silencing and upregulated after BMP4 overexpression.
Figure 5B:
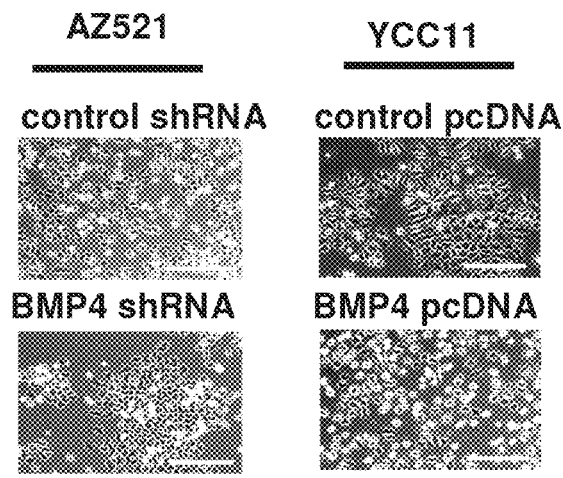
FIG. 5B shows the cellular morphologies of BMP4-manipulated cell lines. It can be seen from FIG. 5B that BMP4-silenced cells show enhanced cell clustering while BMP4-overexpressed cells show enhanced cellular dissociation.

This example demonstrates the potential mechanisms underlying the ability of BMP4 to influence pro-oncogenic traits. Gene expression profiles of BMP4-manipulated lines were generated and compared to parental controls as shown in FIGS. 5A and 5B.

342 genes differentially expressed between BMP4-silenced and parental cells were identified as shown in Table 3 (FDR<10%, 2 fold change). Gene ontology (GO) analysis showed that genes downregulated after BMP4 silencing were significantly related to mesenchymal development (FGFR2, FGF9, VEGFA; p-value<0.01) and TGF-β signaling (SMAD9, FOXP1, FOXP2, ACVR2A, ACVR2B; p-value<0.01). Conversely, among 869 genes differentially expressed between BMP4-overexpressing YCC11 cells and their parental counterparts (FDR<10%, 2 fold change), a significant upregulation of genes related to mesenchymal development following BMP4 overexpression (FGFR2, SOX9, BCL2, HOXA5; p-value<0.01) was observed as shown in Table 3. BMP4 overexpression also caused a significant downregulation of genes related to apoptosis/cell death (HTATIP2, TUBB2A, RPS27L; p-value<0.01), and cell adhesion/junction proteins (MPZL3, CTNNAL1, CASK/CAV2, KCNJ15, LIMS1; p-value<0.01).

TABLE 3

Gene Ontology analysis of genes differently expressed in BMP4-silenced AZ521 and BMP4-over-overexpressing YCC11 cell lines.

| YCC11 pcDNA BMP4 | | AZ521 shRNA BMP4 | |
|---|---|---|---|
| up-regulated genes (p-value < 0.01) | down-regulated genes (p-value < 0.01) | down-regulated genes (p-value < 0.01) | up-regulated genes (p-value < 0.01) |
| mesenchymal development (GO:0060485; GO:0048762; GO:0014031) | endoplasmic reticulum-Golgi apparatus and vesicle-mediated transport (GO:0005783; GO:0044432; IPR000886; GO:0005788; GO:0042175; GO:0005789; GO:0016192; GO:0005794; GO:0005793; GO:0031988; GO:0031410; GO:0042598; GO:0044431; GO:0048193; GO:0030176; GO:0044433; GO:0000139) | mesenchymal proliferation (0002053; GO:0010464) | endoplasmic reticulum and vesicle transport (GO:0016192; GO:0051082; GO:0006897; GO:0048193; GO:0030176) |
| | apoptosis and cell death (GO:0010941; GO:0043067; GO:0042981; GO:0043067; GO:0043068; GO:0012502; GO:0010942; GO:0043065; GO:0006917; GO.0016265; GO:0008219; GO:0006915; GO:0012501; GO:0008629) | TGF-beta signaling pathway (P00052) | p53 pathway (hsa04115; P00059; P00006) |
| | cell adhesion and junction (GO:0007160; GO:0005912; GO:0070161; GO:0030155; GO:0045785; GO:0030055; GO:0007155; GO:0010811; GO:0005924; GO:0010810) | | desmosome (hsa04530; IPR009122; GO:0030057; hsa04510) |
| | response to drug (GO:0042493) | | ubiquitin pathway (GO:0051439; GO:0051438; GO:0051436; GO:0051443; GO:0051444; GO:0006511; P00060) |
| | | | negative regulation of cell motion (GO:0051271; GO:0030336) |

Figure 5C:
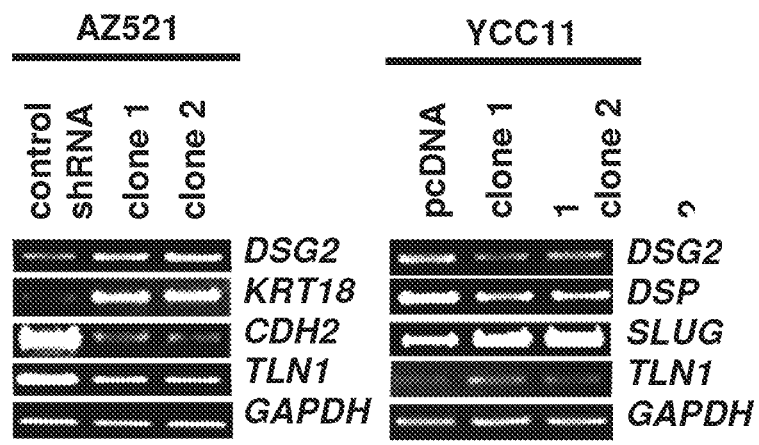
FIG. 5C shows gene expression analysis of molecular markers associated with epithelial-mesenchymal transition. It can be seen from FIG. 5C that the expression of epithelial markers DSG2 and DSP is decreased while the expression of mesenchymal markers SLUG and TLN1 is increased when BMP4 is overexpressed and vice versa.

Epithelial-mesenchymal transition (EMT) is a process activated in many different cancer types to facilitate aggressive invasion and metastasis. Accordingly, the finding that mesenchymal genes are commonly regulated in a reciprocal manner by BMP4 silencing and overexpression evidences that BMP4 facilitates EMT in GC. The role of BMP4 in EMT was investigated by analyzing the phenotypic effects of BMP4 expression on cell morphologies and molecular markers of EMT. One defining feature of EMT is the loss of cell junctions, which allows cells to migrate and invade. AZ521 cells, which express high levels of BMP4, normally exhibit poor cell-cell adhesion. Upon BMP4 silencing, AZ521 cells showed an increased level of cell-cell adhesion, increased expression of the epithelial markers DSG2 and KRT18, and down-regulation of the mesenchymal markers CDH2 and TLN1 as seen in the left panel of FIG. 5C. Conversely, parental YCC11 cells, which express low levels of BMP4, exhibited frequent cell-to-cell attachment to one another. In contrast, BMP4 overexpressing YCC11 cells exhibited rounded morphologies with a striking degree of cellular dissociation, transcriptional down-regulation of the epithelial markers DSG2 and DSP and increased expression of the mesenchymal markers SLUG and TLN1, as shown in the right panel of FIG. 5C.

Taken collectively, these results demonstrate a role for BMP4 in facilitating EMT in GC.

Example 6

This example demonstrates the expression of BMP4 in the clinical setting. BMP4 expression levels in cohorts of primary gastric cancers and other gastrointestinal tumours were examined. BMP4 expression levels in cohorts of primary gastric cancers and other gastrointestinal tumors were examined.

Figure 6A:
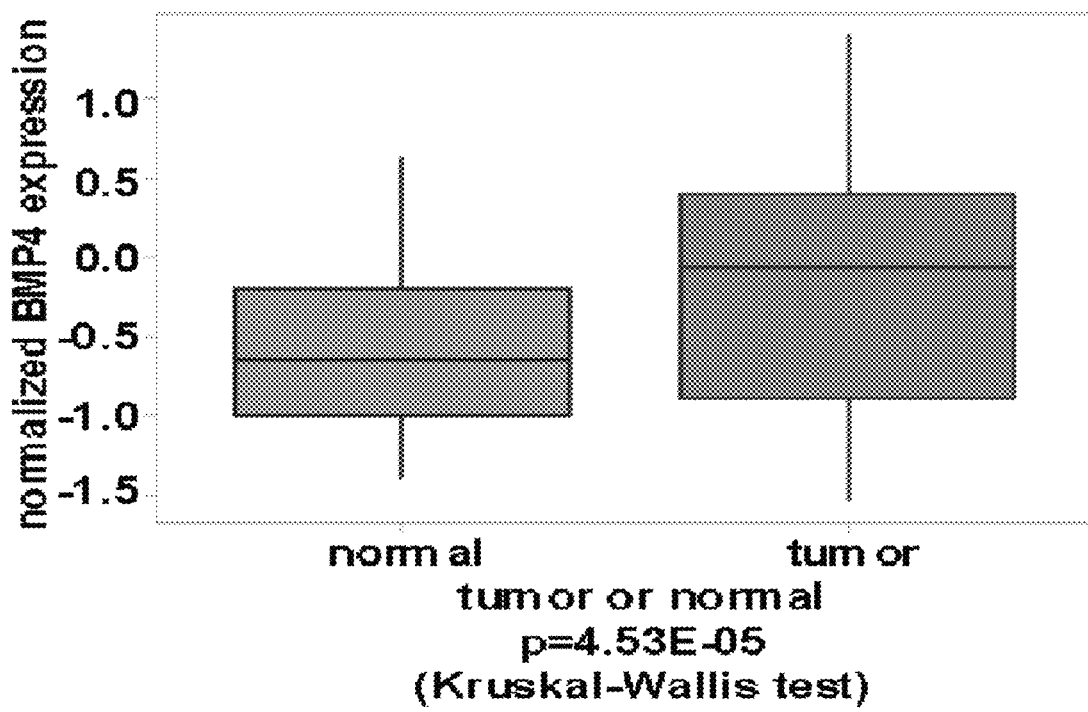
FIG. 6A shows the level of BMP4 expression in tumours compared to normal tissue. Expression of BMP4 is increased in tumors and compared to normal tissue.
Figure 16:
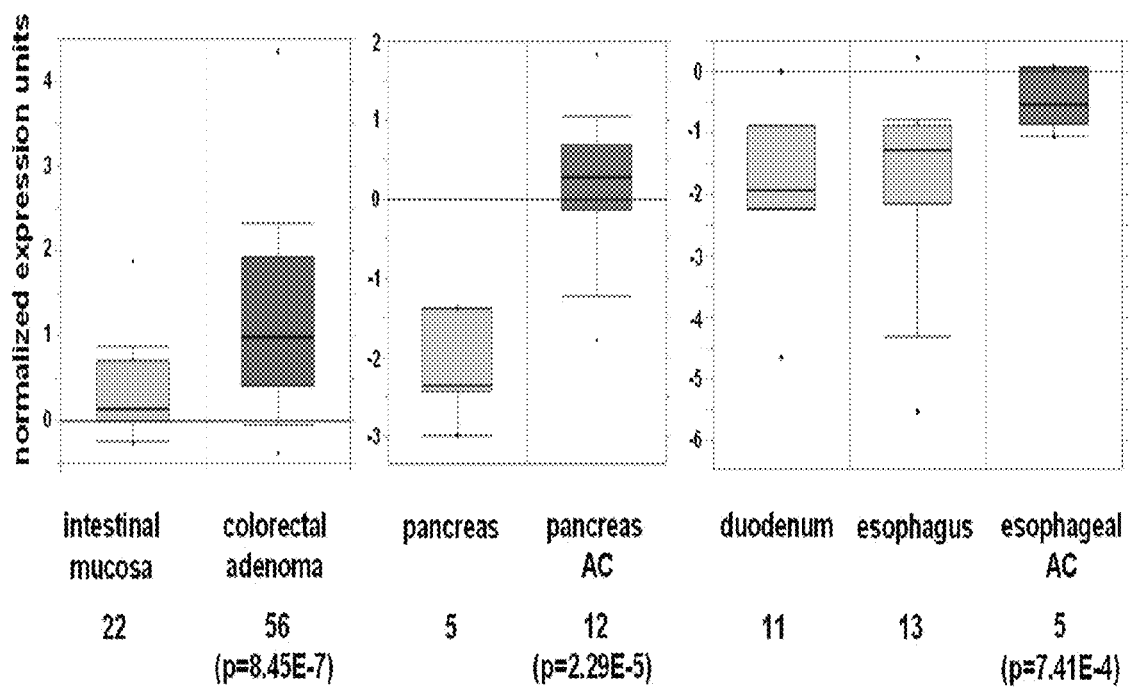
FIG. 16 shows the expression of BMP4 in gastrointestinal tract cancers. BMP4 mRNA expression levels were compared between tumour and non-tumour tissues. It can be seen from FIG. 16 that BMP4 expression is repeatedly and significantly overexpressed in several gastrointestinal tumours.

Analyzing a cohort of 197 GCs as shown in Table 4 demonstrated that BMP4 expression was significantly up-regulated compared non-malignant gastric tissues (p-value=$4.53 \times 10^{-5}$; ave 2.25 fold elevated) as seen in FIG. 6A. FIG. 16 shows that BMP4 was also repeatedly and significantly over-expressed in several other gastrointestinal tumors, including colon, esophageal and pancreatic cancer.

TABLE 4

Clinical Characteristics of Gastric Cancer Patients analyzed in this study. Patients were classified by disease stage according to the American Joint Committee on Cancer (6th Edition).

| Clinical characteristics | Gastric cancer samples (N = 197) |
|---|---|
| Age | |
| Range | 23-92 |
| Gender | |
| Male | 129 |
| Female | 68 |
| Lauren's | |
| Intestinal | 100 |
| Diffuse | 76 |
| Mixed | 21 |
| Grade | |
| Moderate to well differentiated | 72 |
| Poor differentiated | 125 |
| Stage | |
| 1 | 32 |
| 2 | 31 |
| 3 | 71 |
| 4 | 63 |

Accordingly, this result demonstrates that high BMP4 expression is a common feature associated with various tumor types in the gastrointestinal tract.

Figure 6B:
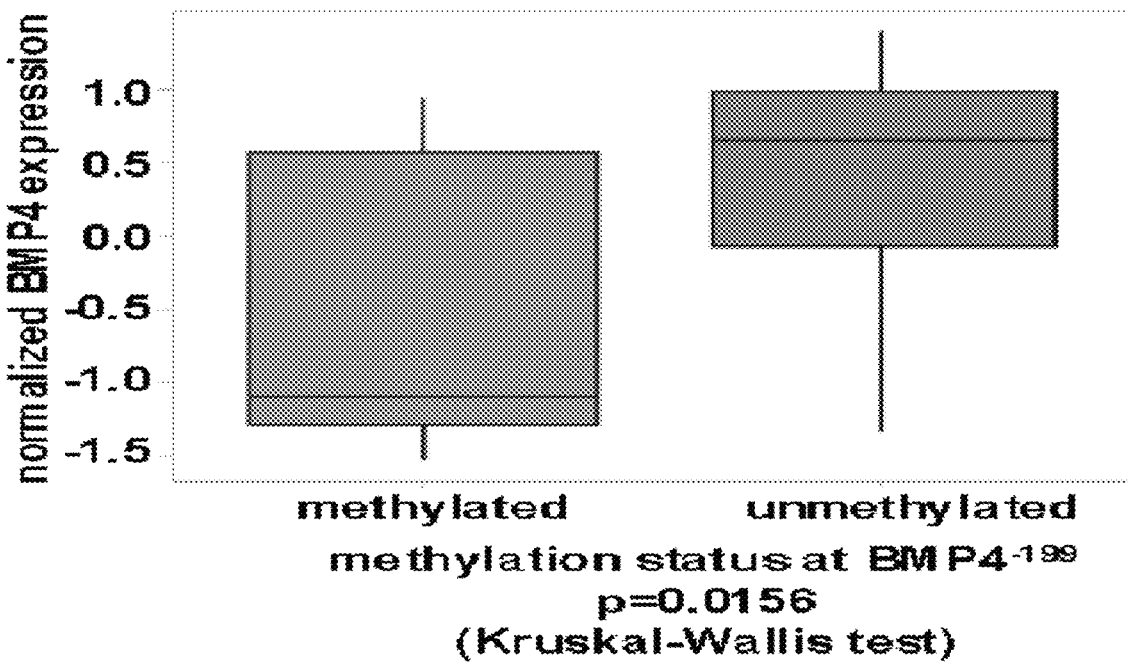
FIG. 6B shows the correlation of BMP4 gene expression to BMP4 methylation in tumours. It can be seen that BMP4 methylation status is associated with BMP4 expression in tumours in vivo.

The primary GCs were ranked by their BMP4 mRNA expression levels to explore relationships between BMP4 methylation and BMP4 expression in primary GCs. 20 tumors with low BMP4 expression and 18 tumors with high BMP4 expression were selected. Genomic DNAs of these 38 tumors were extracted and assayed for methylation at the BMP4$^{-199}$ and BMP4$^{-123}$ sites. Similar to the gastric cell lines, there was a significant correlation between BMP4$^{-199}$ methylation status and BMP4 mRNA expression across the tumors as seen in FIG. 6B and Table 5 (p-value=0.016).

TABLE 5

Correlation of BMP4$^{199}$ methylation and BMP4 expression in gastric cancer cell lines and primary tissues. BMP4 positive and BMP4 negative groups were defined by the median BMP4 expression level.

| | cell lines | | primary samples | |
|---|---|---|---|---|
| | sample number | samples with methylated BMP4-$^{199}$ | sample number | samples with methylated BMP4-$^{199}$ |
| BMP4 positive group | 9 | 1 | 18 | 10 |
| BMP4 negative group | 11 | 10 ($\chi^2$ = 0.0004; p-value = 0.0001) | 20 | 17 ($\chi^2$ = 0.033; p-value = 0.02) |

Methylation of the BMP4$^{-123}$ site was also significantly correlated with BMP4$^{-199}$ methylation (Fisher exact test, p-value<0.01), and tended to be negatively associated with BMP4 expression.

Accordingly, these results establish that BMP4 methylation, specifically at the BMP4$^{-199}$ CpG island, is significantly associated with BMP4 expression in tumors in vivo.

The relation of expression levels of BMP4 to patient survival was assessed to determine the clinical relevance of BMP4 expression in gastric cancer. Based on the median level of BMP4 expression, all 200 GC patients were stratified into "BMP4 high" and "BMP4 low" groups, and the overall survival of these two groups were compared.

The results shown in FIG. 6C demonstrate that patients with tumors expressing high BMP4 levels exhibited poorer overall survival compared to patients with tumors expressing low BMP4 (p=0.016). No other significant clinical-pathologic associations with BMP4 expression were found in GC patients. In a multivariate analysis where BMP4 expression levels were considered with tumor stage, the gold standard for survival stratification in GC, BMP4 still retained its prognostic significance (p-value=0.003; HR=1.533; 95.0% CI: 1.158 to 2.030) as seen in Table 6.

TABLE 6

Cox regression analysis for tumor stage (TNM classification) and BMP4 expression.

| | | | (95% CI) | |
|---|---|---|---|---|
| variable | p-value | hazard ratio | lower | upper |
| multivariate analysis | | | | |
| BMP4 expression | .003 | 1.533 | 1.158 | 2.030 |
| Stage 1A (ref) | .000 | | | |
| Stage 1B | .274 | .476 | .126 | 1.798 |
| Stage 2 | .609 | .739 | .231 | 2.356 |

TABLE 6-continued

Cox regression analysis for tumor stage
(TNM classification) and BMP4 expression.

| variable | p-value | hazard ratio | (95% CI) lower | upper |
|---|---|---|---|---|
| Stage 3A | .164 | 2.118 | .736 | 6.094 |
| Stage 3B | .019 | 3.801 | 1.240 | 11.648 |
| Stage 4 (M0) | .011 | 4.266 | 1.404 | 12.965 |
| Stage 4 (M1) | .000 | 9.068 | 3.024 | 27.191 |
| univariate analysis | | | | |
| BMP4 expression | .016 | 1.387 | 1.062 | 1.811 |
| Stage 1A (ref) | .000 | | | |
| Stage 1B | .457 | .607 | .163 | 2.261 |
| Stage 2 | .932 | .951 | .303 | 2.990 |
| Stage 3A | .107 | 2.372 | .829 | 6.785 |
| Stage 3B | .007 | 4.578 | 1.504 | 13.940 |
| Stage 4 (M0) | .007 | 4.579 | 1.510 | 13.884 |
| Stage 4 (M1) | .000 | 10.690 | 3.597 | 31.773 |

Gene set enrichment analysis (GSEA) of the "BMP4 high" tumours revealed enrichment of several gene sets related to EMT-associated pathways, including cell adhesion (p-value=0.002), hedgehog signalling (p-value<0.001), and TGF-β signalling (p-value<0.05).

Interestingly, the "BMP4 high" tumours also exhibited expression of genes related to cisplatin resistance, including nucleotide excision repair (p-value=0.02) and genes upregulated in gastric cell lines with acquired cisplatin resistance.

Accordingly, these results indicate that BMP4-expressing tumors are associated with poor patient prognosis in GC and a clinical subpopulation for which alternative therapies is needed.

Example 7

This example demonstrates the manipulation of levels of BMP4 activity to modulate cisplatin sensitivity and resistance in gastric cancer to investigate alternative therapeutic options for BMP4-high gastric cancers.

Figure 7A:
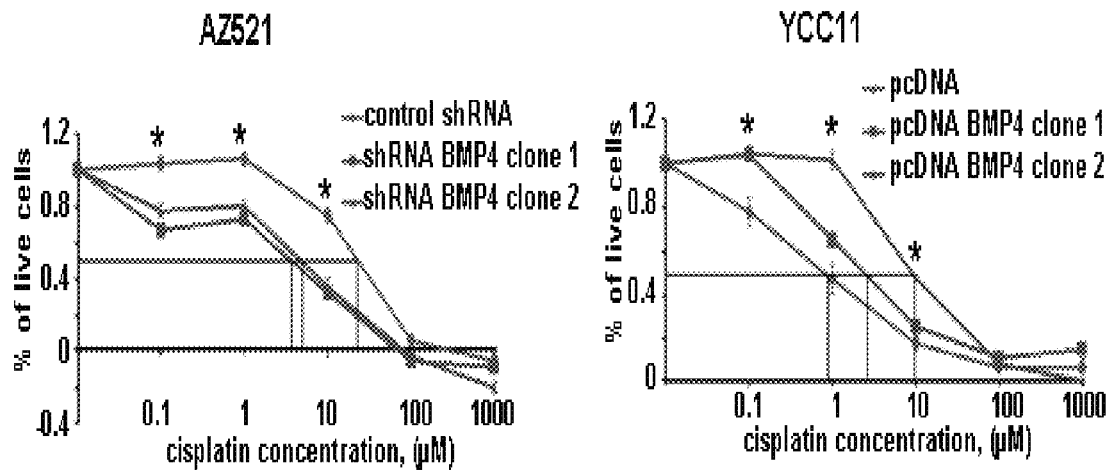
FIG. 7A shows cisplatin-mediated growth inhibition curves for BMP4-silenced and BMP4-overexpressing cells. Cells were treated with increasing concentrations of cisplatin and it can be seen from FIG. 7A that BMP4-silenced cells show enhanced cisplatin sensitivity and BMP4-overexpressing cells show increased cisplatin resistance.

BMP4-manipulated cells were treated with increasing doses of cisplatin as shown in FIG. 7A. Compared to parental AZ521 cells originally defined as cisplatin-resistant, BMP4-silenced AZ521 cells exhibited significantly increased cisplatin sensitivity (p-value<0.01), with a 9-fold decrease in absolute GI50 from 15 μM to 1.1-3.24 μM (individual clones 1 and 2).

Figure 7B:
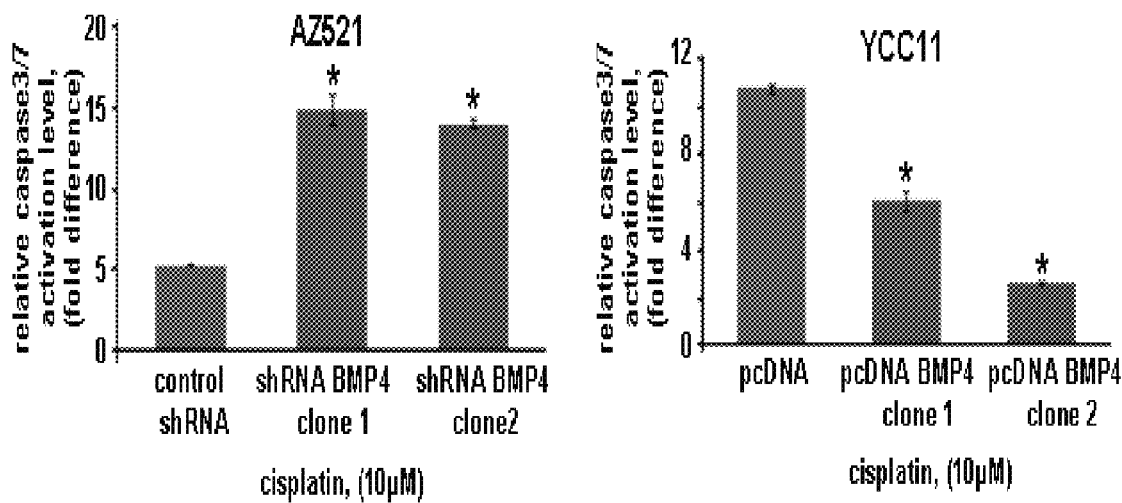
FIG. 7B shows cisplatin mediated cell death in BMP4-silenced and BMP4-overexpressing cells. From FIG. 7B, it can be see that BMP4-silenced cells exhibit higher caspase 3 activation levels while BMP4-overexpressing cells show significantly lower caspase 3 activation levels.

Notably, in these experiments, BMP4 effects on cisplatin sensitivity were distinguished from effects on baseline growth by normalizing the treated cells to their untreated cellular counterparts. Similar to the cellular proliferation data, BMP4-silenced AZ521 cells significantly higher Caspase-3 activation levels after cisplatin treatment compared to control cells as seen in the left panel of FIG. 7B. Reciprocally, compared to parental YCC11 cells originally defined as cisplatin sensitive, BMP4 overexpression caused YCC11 cells to exhibit cisplatin resistance, with a 10-fold increase in absolute 0150 from 45 nM to 0.2-0.5 μM (individual clones 1 and 2), and a reduction in active Caspase-3 levels in BMP4-overexpressing, as shown in the right panel of FIG. 7B.

Accordingly, these results demonstrate that targeted inhibition of BMP4 signaling represents a therapeutic option for sensitizing GC cells to cisplatin treatment.

The invention claimed is:

1. A pharmaceutical composition comprising an anti-cancer drug and an inhibitor of bone morphogenetic protein 4 (BMP4) gene expression and/or an inhibitor of bone morphogenetic protein 4 (BMP4), wherein the anti-cancer drug excludes oxaliplatin and derivatives thereof, wherein the inhibitor of BMP4 gene expression is an interfering ribonucleic acid, wherein the interfering ribonucleic acid is a shRNA comprising the sequence selected from the group consisting of 5'-TGAGGTGACTCACCTCCATCAGACTCGGA-3' (SEQ ID NO: 23) and 5'-GCCACTCGCTCTATGTGGACTTCAGCGAT-3' (SEQ ID NO: 24), or functional variants thereof.

2. The pharmaceutical composition of claim 1, wherein the anti-cancer drug is an anti-cancer drug comprising platinum-complexes.

3. The pharmaceutical composition of claim 2, wherein the anti-cancer drug is cis-diamminedichloroplatinum (II) (CDDP, cis-platin), or carboplatin or a derivative thereof.

4. The pharmaceutical composition of claim 1, wherein the anti-cancer drug is a drug used for the treatment of cancer selected from the group consisting of lung cancer, testicular cancer, breast cancer, colon cancer, ovarian cancer, head and neck cancer, esophageal cancer and gastric cancer.

5. The pharmaceutical composition of claim 4, wherein the anti-cancer drug is an anti-gastric cancer drug selected from the group consisting of cisplatin.

6. A method of treating a patient suffering from cancer by administering a pharmaceutical composition of claim 1.

7. The method of claim 6, wherein the cancer is selected from the group consisting of lung cancer, testicular cancer, breast cancer, colon cancer, ovarian cancer, head and neck cancer, esophageal cancer and gastric cancer.

8. The method of claim 7, wherein the cancer is gastric cancer.

* * * * *